United States Patent [19]

Hudson et al.

[11] Patent Number: 5,591,646

[45] Date of Patent: Jan. 7, 1997

[54] METHOD AND APPARATUS FOR PEPTIDE SYNTHESIS AND SCREENING

[75] Inventors: Derek Hudson, San Anselmo; Charles R. Johnson, Berkeley; Lutz Giebel, Burlingame, all of Calif.

[73] Assignee: Arris Pharmaceutical, San Francisco, Calif.

[21] Appl. No.: 939,065

[22] Filed: Sep. 2, 1992

[51] Int. Cl.[6] .......................... G01N 33/543; C07K 17/00
[52] U.S. Cl. ......................... 436/518; 436/501; 436/528; 436/529; 436/530; 436/531; 530/333; 530/334; 530/335; 422/99; 422/100; 422/104
[58] Field of Search ........................... 422/99, 100, 104; 435/7.1, 7.92; 436/501, 518, 528, 529, 530, 531; 530/333, 334, 335; 536/18.5, 18.6, 253

[56] References Cited

U.S. PATENT DOCUMENTS

| | | | |
|---|---|---|---|
| 4,631,211 | 12/1986 | Houghten | 428/35.5 |
| 4,728,502 | 3/1988 | Hamill | 422/116 |
| 5,010,175 | 4/1991 | Rutter et al. | 530/334 |
| 5,100,626 | 3/1992 | Levin | 422/100 |
| 5,143,854 | 9/1992 | Pirrung et al. | 436/518 |
| 5,188,733 | 2/1993 | Wang et al. | 210/321.84 |

FOREIGN PATENT DOCUMENTS

| | | |
|---|---|---|
| 86/00991 | 2/1986 | WIPO . |
| WO9015070 | 12/1990 | WIPO . |

OTHER PUBLICATIONS

Frank et al., "Facile and rapid 'spot–synthesis' of large numbers of peptides on membrane sheets", pp. 151–152 in *Peptides* 1990, ed. by Giralt et al., (1991) ESCOM Science Publishers B.V.

Wang et al., Peptide Research, vol. 5, No. 5, pp. 275–280, (Sep.–Oct. 1992) "Multiple Peptide Synthesis on Polypropylene Membranes for Rapid Screening of Bioactive Peptides".

(List continued on next page.)

*Primary Examiner*—Lora M. Green
*Attorney, Agent, or Firm*—Oblon, Spivak, McClelland, Maier & Neustadt, P.C.

[57] ABSTRACT

Method and apparatus for simple and rapid preparation of reusable, addressable surface-immobilized arrays of biomolecules (libraries) used for screening for interaction with any biologically significant target. A special plate having on its surface a plurality of discreet functionalized substrate areas, typically in arrays of 10×10 to 400×400, is provided for chemical synthesis or bonding thereon of desired families of biomolecules (e.g. peptides, DNA, RNA, oligosaccharides). In the case of peptides, such as hexapeptides, the resulting permanently hexapeptide-loaded plate is a reusable Addressable Synthetic Peptide Combinatorial Library (ASPCL), in which 1 to 3 (typically two) of the positions in the sequence are uniquely identified by the address location. Plate embodiments include substrates of physically bonded (e.g. glued) conventional particulate materials such as Pepsyn-K, or functionalizable films of linear or crosslinked polymers covalently attached to, or physically adhered to the plate surface. Spacer arm moieties may also be attached to the substrates. A unique multi-slot block assembly is used to prepare the ASPCLs. In library applications, for example determining peptides which bind to functional proteins (enzymes, receptors, antibodies), the substrate-bound peptides are assembled with several positions consisting of uniformly distributed equimolar mixtures of residues, and 2 separated or sequential positions uniquely identified by their spatial location on the substrate array, the "address". Following identification of the known residues giving the greatest affinity for the arrayed positions in the sequence, optimal binding for the complete peptide sequence is determined by an iterative process replacing formerly mixed positions with known AAs at unique addresses.

25 Claims, 2 Drawing Sheets

OTHER PUBLICATIONS

Light–Directed, Spatially Addressable Parallel Chemical Synthesis by Stephen P. A. Fodor, J. Leighton Read, Michael C. Pirrung, Lubert Stryer, Amy Tsai Lu, and Dennis Solas, Research Article, Feb. 15, 1991, p. 767.

Generation and Use of Synthetic peptide Combinatorial Libraries for Basic Research and Drug Discovery by Richard A. Houghten, Clemencia Pinilla, Sylvie E. Blondelle, Jon R. Appel, Colette T. Dooley and Julio H. Cuervo, Nature, vol. 354, Nov. 7, 1992, p. 84.

Science and Technology—The Silver Shotguns, The Economist, Dec. 14, 1991 p. 119.

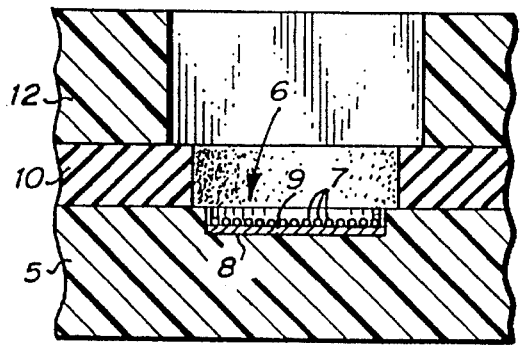
Fig_2a
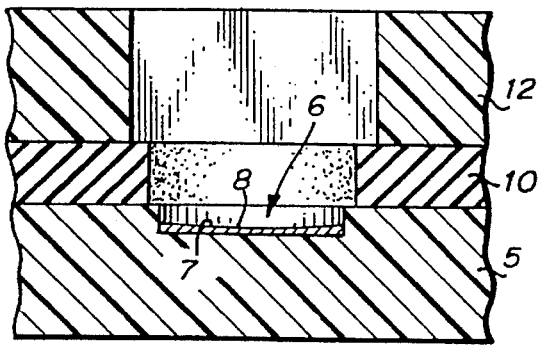
Fig_2b
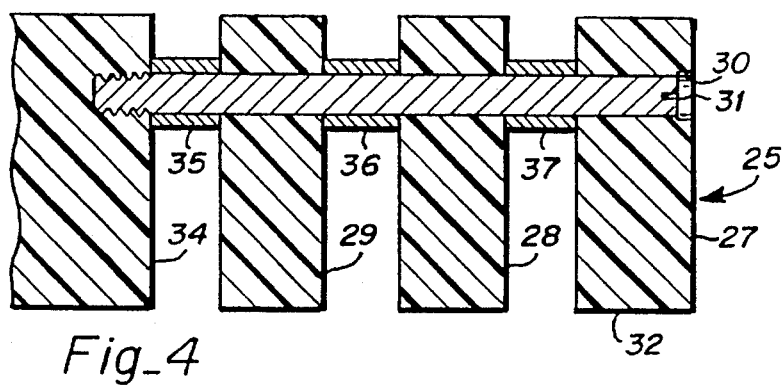
Fig_4
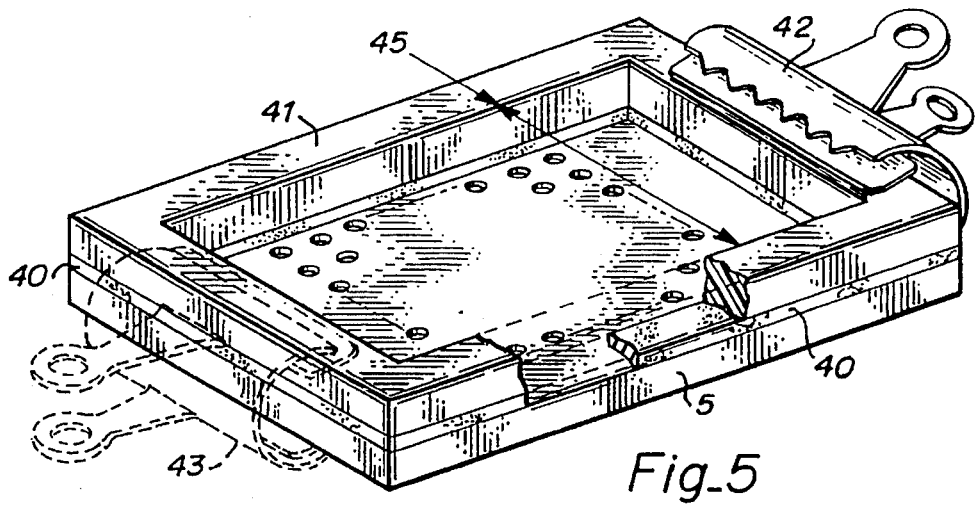
Fig_5

1

METHOD AND APPARATUS FOR PEPTIDE SYNTHESIS AND SCREENING

SPECIFICATION

FIELD

This invention relates to methods and apparatus for preparing a non-volatile, reusable, Addressable Synthetic Biopolymer Combinatorial Library (ASBCL) having known sequences at identifiable designated addresses arrayed on a permanent substrate, which library is rapidly creatable by a unique and simple slotted block system. The invention also relates to the use of ASBCLs to screen for sequences having biologic, biochemical, biomedical or therapeutic activity relative to a specified target. The invention permits rapid optimization of leads for identification of active components. When applied to the specific area of peptides. The invention may be termed PILOT, for Peptide Identification and Lead Optimization Technique.

BACKGROUND

Moderate length peptides have attracted considerable research and commercial interest by virtue of the properties some exhibit in enhancing, blocking or otherwise affecting the activity of receptors, microbes, and other molecules deemed biologically significant. Specifically, hexapeptides have proven to have a sufficient chain length to block much larger molecules such as receptors, enzymes and antibodies. Thus, synthetic and natural hexapeptides have exhibited diverse therapeutic properties, among them: Antimicrobials with minimum inhibitory concentrations an order of magnitude less than known natural antimicrobial peptides; bactericides; antivirals; activity as antigenic determinants; and the like. The problem is that there are 64 million (64 m) hexapeptide combinations for the twenty L-amino acids, and another 64 m for the D-amino acids. Indeed if the selection were made from all of the L and D combinations the number amounts to 4.096 billion. Since there are in turn millions of biologically/medically significant targets, preparing a complete suite of just 64 m L-hexapeptides and assaying activity for each of the millions of targets is, practically speaking, an infinite, and therefore, impossible, task.

Accordingly, the Synthetic Peptide Combinational Library (SPCL) approach has recently resulted in a manageable approach to the problem of screening for a unique hexapeptide among the 64 m that is the most active for a given target. In order to be feasible, libraries of large numbers of hexapeptides, on the order of 100,000 or so at a time, must be prepared in quantities sufficient to result in a positively determinable reaction.

There are currently four basic library techniques offered: viral approachs (originated by George Smith of LSU, and by Cetus and Affymax independently); the Houghten approach using Tea-bags; the Selectide bead approach; and the Affymax Chip approach. The latter three have distinct advantages over the viral approach in which peptide libraries are displayed by bacteriophages (viruses that prey on bacteria). A short degenerate oligonucleotide encoding all combinations of a short peptide sequence is cloned into Gene III or XIII of a filamentous phage and expressed on the phage surface. Recombinant phage are screened with the target molecule (e.g. receptor), and phage expressing a certain peptide that binds to the target are identified. Nucleotide sequence analysis of the recombinant Gene III or Gene XIII identifies the peptide sequence displayed by the binding phage.

The problem with the viral approach is that the range of peptides is limited to those tolerable by virus and *E. Coli.* That is, only a limited suite of peptides can be produced from among the 64 m possible hexapeptides, and likewise for the even greater numbers of longer peptides. Additionally, only L- amino acids are allowed, and each individual hexapeptide of the library is produced within the phage as fusion products. This reduces the flexibility of the sequences, and may mask them entirely.

The Selectide bead approach uses vast quantities of spherical crosslinked polymer beads (Millipore or Cambridge Research Laboratories polyacrylamide beads or Rapp Tentagel polystyrene) divided into 20 equal piles, each of which then has a different L-amino acid coupled to all the beads in the pile. The bead piles are then combined and thoroughly mixed. The resulting single pile is again divided into 20 different piles, each of which is reacted with a different one of the 20 different L-amino acids. This Divide, Couple and Recombine process (DCR) is repeated through six reactions to produce hexapeptides bound to the beads. The beads are then screened against a "target" molecule which is marked with a conjugated enzyme, such as horseradish peroxidase. The target "sticks" to active hexapeptide(s). The bead is rendered visible by adding a substrate for the enzyme which converts it to a colored dye which is precipitated within the beads, and then the visually identified bead(s) are picked out with tweezers. The peptides on the beads are then analyzed, for example by the Edman sequencing method, and soluble versions produced in a synthesizer. The initial screening (locating the target bead(s)) takes only days, the makeup of each identified hexapeptide is unknown, and the analysis and synthesis for confirmation and further work takes much longer.

The Houghten (Iterex) Tea-Bag method, shown in U.S. Pat. No. 4,631,211, employs methylbenzhydrylamine (MBHA) polystyrene beads in a number of foraminous containers, e.g. porous polypropylene bags (Tea-Bags), to prepare a truncated SPCL. In order to shorten the processing time, the Tea-Bag process employs partially known, partially undetermined hexapeptide sequences in repeated screenings, followed by iterative resynthesis to replace the unknown AA sequence positions with known AAs, i.e., A-$O_1O_2O_3$XXX, A-$O_1O_2O_3O_4$XX, etc. The method works on the assumption that a biologically significant response can be detected from a solution which contains hundreds of thousands of inactive components.

The Tea-Bag process typically uses 18 of the 20 L-AAs (cysteine and tryptophane are omitted in the initial library for ease of synthesis), starting with 104,976 combinations of non-determined tetrapeptide resins (XXXX-peptide resins) in 324 aliquots, and adds the 324 known dipeptide sequences ($18^2$) in the terminal two positions. For epitope determination of antibody binding, the 324 pools are screened to see which best inhibits binding of the target antibody with its natural antigen. The most active amino terminal dipeptide sequences are then incorporated into a further set of 20 pools in which the third residue is varied. These are rescreened for low IC. The most active sequences are again reincorporated iteratively to define positions 4-6 to finally obtain a characterized active hexapeptide.

The Tea-Bags employ MBHA-styrene beads and standard t-Boc chemistry (the conventional Merrifield method) in combination with simultaneous multiple peptide synthesis (SMPS) to prepare the starting $18^4$ non-determined XXXX-tetrapeptide library by a DCR process, which assures equimolarity of the peptides on the resin. Briefly, 18 porous polypropylene packets, each containing 4.65 mmol (5.00 g) of MBHA resin, are coupled with each of the protected N-x-t-Boc amino acids. Coupling reactions are checked to ensure they are complete (>99.5%) as assessed by Gisin's picric acid or Kaiser's tests. The resulting resins are then combined and thoroughly mixed as with the Selectide bead process. The resulting resin mixture is separated into 18 portions of equal weight which are placed into porous polypropylene packets, followed by N-a-t-Boc protecting group removal and neutralization of the resulting amine TFA salts. The resin packets are then reacted with solutions of the individual activated amino acids to yield the 324 dipeptide combinations ($18^2$). The above DCR process is repeated twice more, yielding a final mixture of 104,976 protected tetra-peptide resins ($18^4$). This XXXX-resin is divided into 324 aliquots (150 mg each) and placed in numbered porous polypropylene packets. Synthesis of the next two defined positions is carried out by SMPS. The peptide mixtures are deprotected and cleaved from their respective resins using low-high hydrogen fluoride (HF) in a multiple HF cleavage apparatus (Multiple Peptide Systems, San Diego, Calif.). Extraction of the individual peptide mixtures was carried out with $H_2O$. The competitive ELISA used is a modification of the direct ELISA technique, differing only in the antibody additions step in which 25 microliters each peptide mixture of the SPCL was added with a fixed dilution of the antibody (25 microliters per well).

The foraminous container of the Tea-Bag must retain the solid phase beads, yet have a sufficient number of openings to permit ready entrance and exit of solvent and solute molecules at the reaction temperature, but bar exit of the solid phase. While the synthesis is the standard Merrifield technique, new linking groups that attach the $X_n$-peptide to the styrene bead supports are disclosed. This process can be characterized as not calling for a continuous support, and it is not addressable.

The Affymax "chip" approach is described in PCT publication W090/10570, which discloses a method for multiple peptide synthesis on a solid support. Photolabilely-blocked amino groups are chemically attached (bonded) to a silicon chip, then irradiated through a patterned mask to selectively remove the blocking groups in a pre-arranged pattern. An amino acid will bond by addition only to the irradiation exposed areas. Additional masks are imposed and radiation applied as a prelude to adding second amino acids. Each amino acid added can include a blocking group so that further addition to that site occurs only after irradiation unblocking. Repeating the process with plural masks builds location specific polypeptides. When the chip is exposed to the target molecule, it may stick to one or more locations. By checking coordinates on a map of the chip, the peptide is identified. However, this process does not work with target molecules stuck to, or part of, cells, and there are exposure problems during processing, i.e., some AA's are light sensitive and cannot be used. Further, the reactions at the surface are not complete; for example, where reaction completion is only 90%, by the 6th iteration to obtain a hexapeptide, only half of them will be made properly.

Accordingly, there is a need in the art for a peptide synthesis and screening process that is rapid and accurately identifies the active peptides from amongst those in an extended, reusable SPCL.

THE INVENTION

OBJECTS

It is among the objects of this invention to provide methods and apparatus for creating a non-volatile, reusable Addressable Synthetic Biopolymer Combinatorial Library (ASBCL) having known amino acid sequences at identifiable designated addresses arrayed on a permanent substrate for rapid screening of target receptors and molecules.

It is another object of the methods and apparatus of this invention to produce ASBCLs in which the biopolymers are peptides, to provide ASPCLs for use in a Peptide Identification and Lead Optimization Technique (PILOT).

It is another object of this invention to provide an improved addressable substrate for adsorption thereon or bonding thereto of biopolymers, such as peptides in known AA sequences, by means of a slotted block system.

It is another object of this invention to provide a simple slotted block system which permits rapid multiple amino acid addition reactions to build peptides of known sequences at identifiable designated addresses in an X-Y coordinate array on a variety of planar substrates.

Still other objects will be evident from the specification, drawings and claims of this application.

DRAWINGS

The invention is disclosed in more detail with reference to the drawings in which:

FIGS. 2a and 2b are section views taken in elevation along line 2—2 of FIG. 1 showing two alternative structures of a substrate area in detail;

FIG. 4 is a section view of the concentric annular block taken along line 4—4 of FIG. 3; and FIG. 5 is an isometric view of the peripheral frame system of this invention for functionalizing plates prior to condensing biopolymers thereon.

SUMMARY

Figure 1:
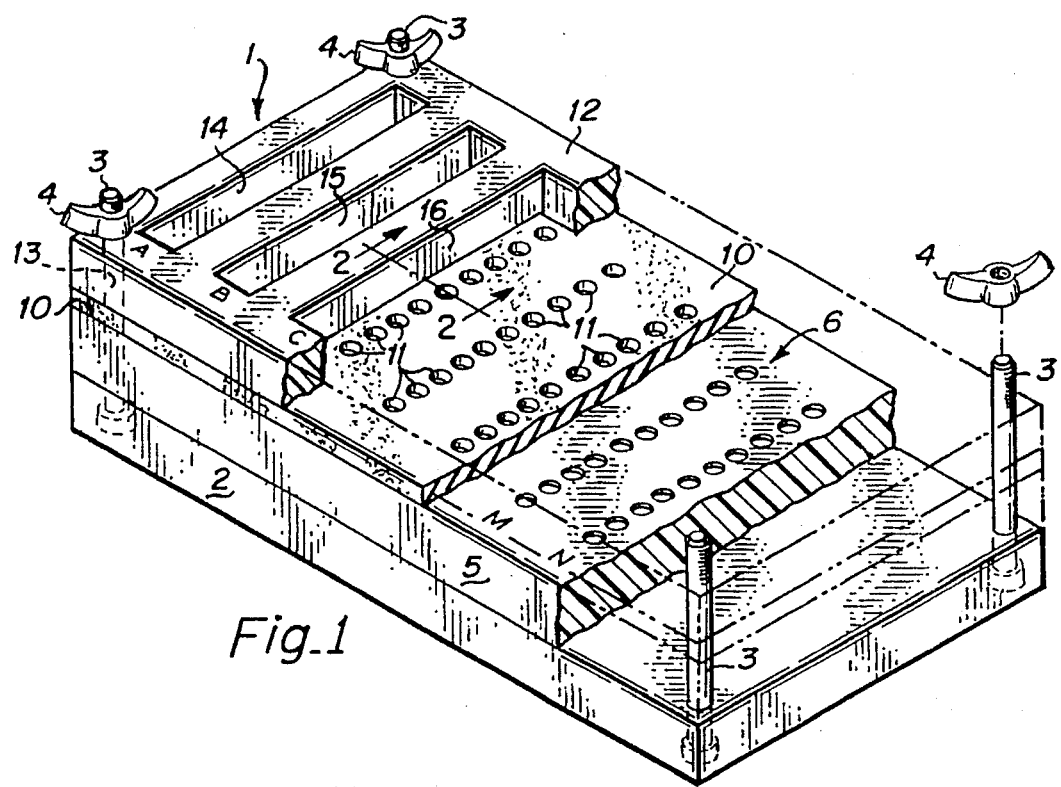
FIG. 1 is an isometric view of an assembled PILOT slotted block system apparatus, partly broken away to show the various parts in proper alignment and ready for introduction of AA's for reaction with the substrate areas or moieties thereon.

The invention comprises methods and apparatus for preparing non-volatile, reusable, Addressable SBCLs (ASBCLs) or SPCLs (ASPCLs), having known arrayed dipeptide amino acid sequences incorporated at any desired and known position within any biopolymer, e.g., polypeptide, sequence of length producible by chemical synthesis methodology, in which up to 6 positions (typically 4) may be composed of mixtures of residues, the remaining positions comprising specified amino acids. The arrayed peptides are identifiable from designated addresses provided on a permanent, reusable substrate which permits creation of an ASPCL, typically within a day. While the discussion herein is with reference to hexapeptides by way of example, the principles of the invention are applicable to any binding determinant biopolymer to produce an ASBCL for interaction with any biologically significant target.

The ASBCLs of this invention can uniquely identify the binding determinant biopolymer, e.g. an active hexapeptide, at a unique X-Y coordinate axis upon bonding with or adhering to a fluorescently labeled, radio-labeled or enzyme linked target molecule or receptor, e.g., in solution flowed into contact with the ASPCL-bearing substrate. The amino acids and peptide sequences are substantially equimolar concentrations on the substrate so good quantitative activity is determinable by the fluorescent or radio intensity, or by the optical density of the dye product formed in the enzyme linked probing.

In addition, the hexapeptide array is permanently bound to the plate i.e., is non-volatile, and at each site on the substrate on the order of 1 μ mole or more can be bonded. The target molecule can be washed off the substrate plate so that it can be reused repeatedly, particularly for diagnostic testing, as well as rapid active peptide screening on a wide variety of target receptors. For example, a preselected library of peptides, or any other condensation chemistry-based screening agent, may be permanently bonded to a substrate as a diagnostic tool. One example involves exposing an ASPCL plate of this invention to one or more aliquots of a serum which requires diagnosis, and then visualizing binding by passing a flourescently or radiolabeled anti-IGG antibody over the ASPCL plate. Consequently, one or more conditions, such as the presence of antibodies to HIV-1, or the presence of other viral infections can be rapidly and simply diagnosed.

More broadly considered, the peptide may be any biopolymer, thus the terms ASBCL applies to the library on the identifiable designated addresses arrayed on the permanent reusable substrate. It should be understood that the term "substrate" as used herein includes broadly: a) polyolefin plate alone or an activated plate plane substrates; b) a plate with a bead or gel substrate, amino functionalized or or bare, (receptor substrate); c) such beads or gels with spacer arms, amino-functionalized or bare, spacer receptor substrates; and d) reacted substrates i.e. such substrates above with one or more AAs or peptides linked thereto.

The apparatus system of this invention comprises employing an inert substrate support plate, such as a polyolefin polymer, having a plurality of discrete sites (preferably small, well-like, shallow flat-bottomed circular or square depressions) in a spaced array, e.g., 10×10, 16×16, 20×20, 40×40, 100×100, 400×400, or any other desired number. Each of the sites are permanent uniquely addressable locations for assembly of the biopolyer chains or attachment of preactivated molecules. Each site includes an amino functionalized substrate media such as glue-bonded beads or chemically grafted polymeric films, which may be gel-type films. Any conventional peptide substrate, media, or addition chemistry-based agent substrate, may be used.

Examples of bead type substrates are polydimethylacrylamide (PDMA) particles, silica beads, MBHA polystyrene beads, and the like, which are glued to the substrate areas of the support plate. The presently preferred bead substrate is Kieselguhr-encapsulated PDMA particles (Pepsyn-K from Milllipore Corp.), secured to a polyethylene plate with a low temperature (<100 degrees C.) hot-melt polyethylene adhesive. The preferred polymeric film is chemically grafted to the surface of the wells by a process disclosed herein, and is particularly useful for screening involving large proteins.

Two methods of attachment of amino-functionalized polymers to form substrate areas on the plates are disclosed by way of examples of the principles of the invention; in situ polymerization (disclosed in detailed examples); and bonding of a pre-polymerized material to activated areas on the plate (disclosed in general). The first polymerizes acryloylated monomers and crosslinking agents onto acryloyl groups attached to the areas of the polyolefin surface (plate activation). This establishes a gel-type polymer covalently grafted into the depressions. This polymer, since it may possess low structural strength, i.e. it need not have high structural strength, can be prepared from monomers at low concentration and with a low molar percentage of crosslinking. The resulting gel substrate materials are therefore highly permeable to proteins, thus greatly improving the sensitivity of detection. The gel film may then be amino functionalized.

A spacer arm derivative is attached to the functional amino groups of the resultant films. These spacer arms, which are also used for the glued beads, increase sensitivity since they reduce unfavorable steric and electronic interactions between the incoming tagged protein and the polymer backbone. An ideal spacer is non-hydrophobic, incapable of forming aggregates by hydrogen bonding, and typically longer than 10A. A variety of materials, including functionalized polyethylene glycols, sugars, and short natural and unnatural peptides may be used as spacers.

The second (pre-polymerized) method of attachment of functional polymers involves attachment of preformed amino-functionalized polymers to the designated areas on the inert support plate (polyolefin). The preformed polymer itself serves as a spacer arm, and access of proteins is improved as compared to the in situ gel type polymers. Examples of preformed amino-functionalized polymers include polyethyleneimine, polyallylamine, long chain functionalized sugars (e.g. dextrans), polyamino acids (e.g. poly-L-lysine) and the like. They can be coupled to acid chloride activated plate areas by reactions of the type described herein. We prefer to use a 500,000 MW dextran that is amino-functionalized pre- or post-attachment to the plate area.

An elastomeric sealing gasket having a plurality of holes therethrough aligned with the substrate areas is placed over the substrate array plate, and a slotted block is placed over the gasketed plate so that individual slots align with rows of substrate areas. Since each area is part of a predetermined array, each defined substrate area has a unique X-Y coordinate address, such as: Row 1, position 1; Row 2, position 20; Row 3, position 78; to Row $X_n$, position $Y_m$. Any desired address system may be used, such as sequential numbers for each succeeding area, dual alpha system (AA, AB, AC etc.), or alpha numeric (A1, A2 . . . B1, B2 . . . ).

The slotted block has a height sufficient to provide a well of sufficient volume to receive reaction solution having selected moieties for bonding with the exposed substrate address area or reaction with a previous moiety. Each well can receive a different reactant, e.g. a blocked AA, so that each row has a different $A_n$ position AA. Next, the reactants are removed from the slots in the block, e.g. by decanting or suction, then the amino blocking group removed by a deblocking agent, e.g. piperidine. Then the block is rotated horizontally 90°, and each slot well receives another, same or different, reactant so that the $A_{n+1}$ position has a predetermined AA. Where the sequence of AAs are the same in each well at each block orientation, turning the block 90° produces all 400 combinations of dipeptides for a 20 slot block/400 substrate area plate system. Iterative application of 3 such plates, two positions being optimized at a time, allows for the identification of the single optimal binding peptide from a 64 m hexapeptide SPCL. The substrate areas can be quite small to provide peptides in adequate (picomolar) amounts.

As an illustration of one method of use of the system of this invention, a random sequence of all XXXX-tetrapeptides on Pepsyn-K beads is prepared, and these beads adhered to the substrate areas. Alternately, a polymeric film gel may be prepared for each area. Then, using the system of this invention, the terminal two AA's can be added thereto in the all-combination 20×20 array, and the hexapeptides exposed to targets. A deductive process involving iterative resynthesis of successively smaller libraries can be used to successively characterize the resulting screening-active hexapeptide. Alternately, the procedure and apparatus of this invention can work from a defined middle dipeptide with random ends, followed by replacement of each end in sequence with known dipeptides. Likewise 4 or 5 residues may be mixed, or an array of any kind of peptide, including those including one or more non-natural AAs, can be employed on the reusable substrate of this invention.

The use of beads adhered to the support address area is preferred for diagnostic or drug use applications, as single preselected known-sequence peptide-containing beads can be prepared and glued to the support in a specified address. Likewise, DNA moieties can be bonded to the support, in which case a 16×16 array, or an array of 16-4×4 subarrays, on a single plate is preferred.

Advantages of the apparatus and methods of this invention include: Synthesis of defined peptides, portions of which optionally can consist of redundant known or unknown (uncharacterized or non-defined sequence) mixtures which are bonded in micromolar amounts in defined arrays with known addresses so that a physical barrier (e.g. an appropriately apertured member) can permit simultaneous screening. Another feature is fluorescent or radiolabeled detection of binding, which provides higher sensitivity and is far more suitable for detection of low affinity interactions than the current Selectide or Iterex technology. The solid array support also permits inference of optional binding elements (e.g. AA sequences) from the spatial position (unique address) rather than requiring chemical determination of sequence.

The ASBCLs and ASPCLs constructed by the method and system of this invention are selectively variable at any two or more positions, while redundant (random selection of all combination) at several other positions (3-6) within peptides or biopolymers of a wide range of size and structure. The system is also useful for screening by itself, or in conjunction with current methods (such as the Iterex Tea-Bag or Selectide methods), for any two or more AA position sequencing, and can be used for progressive refinement of initially identified hits (indications of activity). Because of the effectiveness of the support system of this invention, the separate zones (one or more support address area(s)) can be functionalized for synthesis of peptides at loadings as low as about 0.001 micromoles per cm$^2$, and typically in the range of from about 0.05 to about 50 μ mole/area. The system also permits simultaneous or sequential synthesis by standard Fmoc or t-Boc-chemistry of identified areas (addresses) of distinct known or non-defined peptides, by attaching the slotted block to the substrate plate for simultaneously performing individual separate couplings in the slot compartments. By transforming the block orientation, arrays of peptides may be synthesized at any two positions within a peptide or biopolymer of any length. The previous or following AAs in the peptide sequence may be uniform across the entire substrate surface, and may be unique or consist of mixtures of one or more peptides of known or uncharacterized composition.

While the same block is shown used in different orientations, e.g. rotating a slotted block 90°, two dissimilar blocks may be used in the array generating steps, such as a radial slot block (slots extending radially outwardly from a common center) in combination with a block with concentric circular (annular) slots, and the resultant array may be addressed by polar coordinates.

The system of the invention permits displacing the label on the target with a natural ligand to insure specificity of the identification. It also permits reuse of the substrate for repeated probing of the surface by alternative proteins i.e. exposure to different targets followed by washing. Different areas (addresses) may employ the same or different binding materials, e.g. Pepsyn K particles in one area, and grafted films in another.

Although the method and apparatus shown herein are directed to definition of optimal binding linear hexapeptides, it has great applicability in different formats. Especially where the protein of interest, e.g. cytokine receptor, binds a large ligand, then it is advantageous to insert the library within longer sequences, particularly those which are known to form stable secondary structures, as in loops, beta conformations or alpha helices. In the latter, since the library is then displayed on a cylindrical surface, it is of interest to construct the components 3 or 4 residues apart, the components being separated by helix-forming residues, such as alanine. For libraries based on loop structures, either end may be designated as a Cys residue which can then be coupled together by intramolecual disulfide bridges. Cyclic peptides, especially cyclic hexapeptides and cyclic decapeptides can be constructed on PILOT substrate matrices of this invention, and are especially useful for the relative rigidity of these molecules compared to their linear counterparts.

The novel PILOT ASBCL's and methods of this invention provide distinct advantages over the numerous alternatives discussed above in the Background to meet the need for developing new pharmaceutically useful compounds. The specificity of the binding may be uniquely established by side-by-side comparative processing of dual plates which are then probed, one with the presence of the natural ligand, the other without, and the two compared.

One particular advantage of the invention is that it allows detection by numerous methods, but it is unique in being suitable for detection with radiolabelled derivatives, with autoradiographic and counting methods providing the enhanced sensitivity vital for the detection of relatively low-affinity binding peptides which are present in picomolar amounts within pools containing thousands of other non-binding sequences.

Another advantage of the invention is that it allows for the use of standard particulate substrate materials (e.g. Pepsyn K for peptide synthesis, controlled pore glass for DNA/RNA synthesis), for synthesis on the plates, or for preassembly by automated synthesizers followed by arraying these for diagnostic applications. In library applications, the unique method of grafting in-situ generated polymers or attaching preformed polymers to functionalized polyolefin surfaces provides materials far better suited for screening methods than conventional particulate solids. A special virtue is the optical clarity of the film substrates of this invention, combined with their low intrinsic fluorescence which greatly enhances the sensitivity when used with fluorescent tags. Of even greater importance is that the substrate films of this invention are formulated to provide excellent penetration of proteins within their bounds, and side-by-side comparisons with prior art methods have shown significantly enhanced sensitivity with use of this invention.

This invention is unique in being suitable for construction of libraries containing monomer units of almost any kind, for example, bound together by ether, thioether, ester, amine, phosphate, amide or any such bond establishable by organic chemistry methods. Identification is performed solely through spatial recognition, and does not require sequencing, which is generally impossible with other than natural peptide and DNA units.

The PILOT ASBCL's and methods of this invention, are therefore unique, simple, generally applicable and readily duplicated. They provide high sensitivity detection by a variety of tagging procedures.

DETAILED DESCRIPTION OF THE BEST MODE OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

Referring to FIG. 1 the slotted block system of this invention 1 includes a base 2 which has or receives orienting members, such as a plurality of guide and securing rods 3 with wing nuts 4. The base 2 receives a substrate support plate 5 which includes an array of areas 6. As best seen in FIG. 2a, each area 6 includes substrate 7 (in this case beads) secured in depression 8 by a suitable glue 9. FIG. 2b shows a grafted polymeric film as the substrate 7 in depression 8. Overlying the substrate support plate 5 is a gasket 10, preferably a sheet of chemically inert elastomeric material (e..g. Viton or silicon rubber), having an array of holes 11 therethrough which are in alignment with the substrate areas 6. The gasket functions to prevent leakage between individual substrate areas 6. A slotted block 12, having holes 13 therethrough to receive the guide/securing rods 3 is placed over the gasket 10. This block 12 includes a plurality of slots 13, 14, 15 etc. therein, which are aligned with and extend a full row width of the substrate areas 6. The slots may be identified, as by the alpha designations A,B,C etc. shown. Note in the substrate support plate 5, additional corresponding rows L,M,N . . . are shown. In a typical block 12, there will be some 10 to 400 such slots. Fastening the wingnuts 4 secures the assembly together in the proper orientation and prevents leakage between adjacent slots and substrate areas when individual reaction solutions are placed in the wells formed by the slots. After reaction and removal of solution, upon rotating the block 12 by 90° and reintroducing solutions in the slots, a known array of dipeptide sequences is produced.

Figure 3:
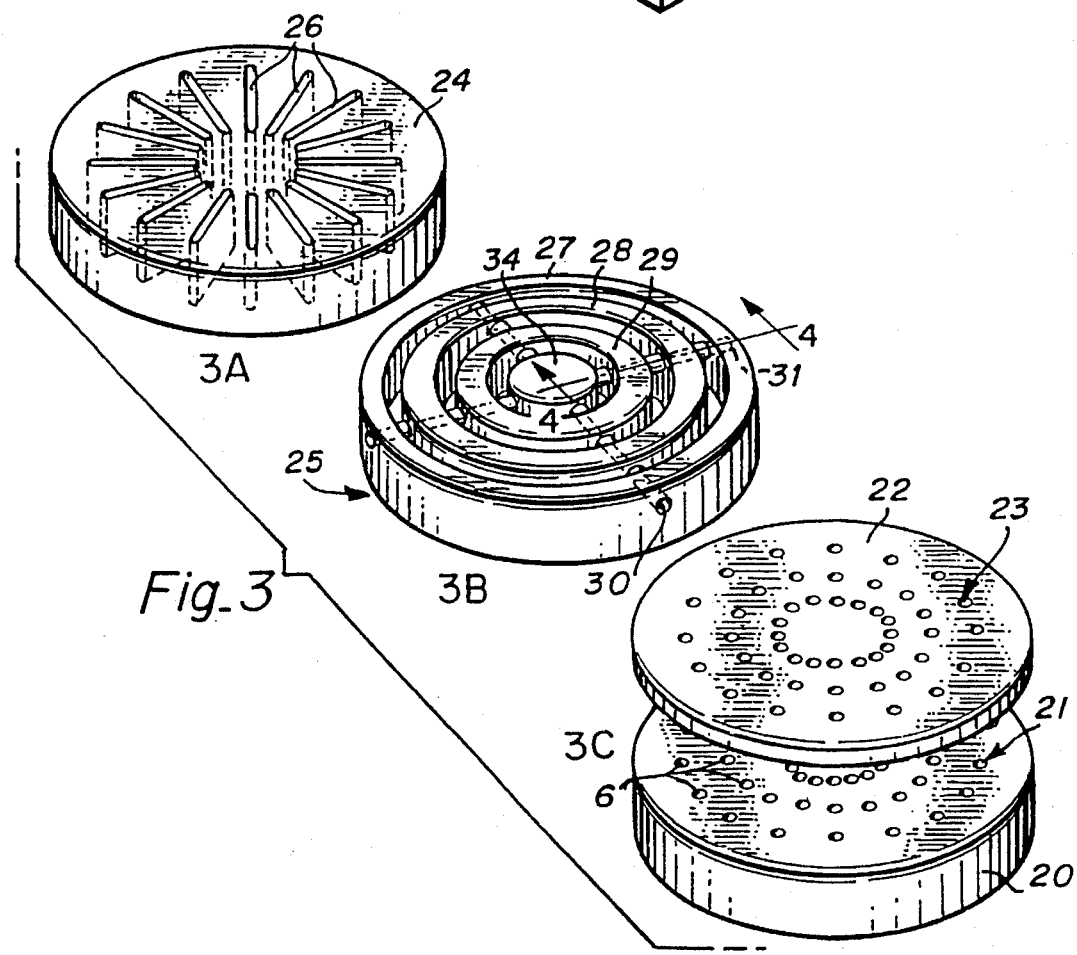
FIGS. 3A, 3B and 3C illustrate using a combination of two different blocks, one radial and one with concentric annular slots, with a circular support plate to produce a circular array.

FIGS. 3A, 3B and 3C show an important variation involving a round substrate support plate 20 having a concentric/radial array 21 of discrete substrate areas 6. A gasket 22 also includes a corresponding concentric/radial array of holes 23. In this embodiment, two slotted plates may be employed sequentially: slotted radial plate 24, and concentric slotted plate 25, in either sequence, 24, 25 or 25, 24. There may be fewer radial slots 26 than the radial array of holes 23 or substrate areas 21, in which case the block 24 may be turned between application of reactants (e.g., AA solutions). The inner concentric segments 27, 28, 29 etc. may be secured in spaced relationship by horizontal rods 30, 31, which are spaced above the bottom 32 of block 25 to insure access of solution to all relevant substrate areas. In FIG. 2 the base plate and pins are omitted for clarity.

FIG. 4 shows in vertical cross section the construction of the concentric slotted plate 25 in which outer ring 33 is spaced from inner core 34 by rod 31. A series of tubular spacers 35, 36, 37, 38 on rod 31 space the concentric intermediate rings 27, 28, 29 to provide concentric annular slots. The rod 31 may be countersunk in bore 39.

FIG. 5 shows a border frame assembly for functionalizing the substrate areas 8 on support plate 5, e.g., with common AAs, or mixtures of AAs, and for deblocking, washing, probing (screening) and addition of spacer arm derivatives. An edge gasket 40 is placed on the substrate plate 5, then a border frame 41 is placed thereover and secured with clamps 42, 43. This provides a central well 45 for the entire array for receiving the appropriate solutions for the functionalizing chemistry.

The following example protocols describe the sequential steps of the method:

EXAMPLE 1

Determination of AA Mixture Proportions for Equimolar Incorporation on Substrate Beads:

The component amino acid (Fmoc-X-OH,1 equivalent) is mixed with Fmoc-Nle-OH (1 equivalent), then dissolved and activated by the addition of PyBOP, HOBt and NMM solutions. After 10 minutes the mixture is added to Nva-PAL-Pepsyn K support (5 mg). After 2 hours the support is washed with DMF repeatedly, treated with 30% piperidine in DMF (to remove incorporated Fmoc- groups), washed with DMF, and methanol, then treated with TFA/water (95:5) for 2 hours. The TFA solution is expelled into a vial, a known proportion of it dried down in vacuo, and the resultant mixed dipeptides X-Nva and Nle-Nva are hydrolysed with 6M HCl at 150 degrees for 1 hour. The relative incorporations of X and Nva are then determined by amino acid analysis. A graph is constructed plotting molar % X (in this initial round X is 50%) against molar percentage incorporated; and the curve which results when using extremities points at 0 and 100% is used to predict what molar percent X would give equal incorporation to that of Nle.

The process is repeated using the predicted molar percent X to confirm and, if necessary, iteratively refine the molar percent. This method has been applied to all 20 natural L-amino acids, most D-amino acids, and several unnatural amino acids, such as beta-alanine and 2-napthylalanine.

For any desired library mixture, the amino acids are selected, mixed in the correct ratios, activated, coupled to the support, and the equal incorporation confirmed by analysis. For the 10 amino acid library the subject of these examples the following recipe gives equal incorporation: Fmoc-L-Nle-OH 0.188 g; Fmoc-L-His(Trt)-OH 0.73 g; Fmoc-L-Pro-OH 0.24 g; Fmoc-L-Gln(Trt)-OH 0.797 g; Fmoc-L-Tyr(tBu)-OH 0.398 g; Fmoc-Gly-OH 0.093 g; Fmoc-L-Phe-OH 0.206 g; Fmoc-L-Arg(Pmc)-OH 1.25 g; Fmoc-L-Glu(OtBu)-OH 0.288 g; and Fmoc-D-Ala-OH 0.130 g. To these mixed amino acids were added HOBt 1.614 g, and the entire solids totally dissolved in DMF and made up to a volume of 40 mL. For coupling, 10 mL of this solution, called MIX solution, is added to 1.71 g PyBOP reagent, mixed, 0.35 mL of N-methylmorpholine is added, remixed and left for 10 minutes. This solution is adequate to completely cover and react a single 10×10 plate giving equal incorporation.

EXAMPLE 2

Preparation of A "Beaded" Plate (Support Plate With Array of Bead-Type Substrate Areas):

The sequence BAla-BAla-BAla-Nle-BAla-Nle-BAla-BAla was assembled on 0.2 mmol/g Pepsyn-K (Millipore)

functionalized by treatment with ethylenediamine using a Milligen/Biosearch model 9600 peptide synthesizer using standard BOP+HOBt coupling protocols. Ace Hardware Hot Melt adhesive was cut into thin sections and melted at as low a temperature as possible on a flat PTFE sheet to produce a thin sheet (in a range of from about 0.2 to about 1.0 mm thick) of hot melt adhesive (HMA sheet). The PTFE sheet was removed from the heat, and dry, peptide-bearing Pepsyn-K beads were sprinkled over the melted glue surface and gently patted down. After several hours of cooling, excess beads were removed and the glue sheet lifted off the PTFE sheet, then punched into appropriate circles (e.g. 1–10 mm dia) with a standard hole punch. The resultant discs were then attached to an array of shallow, dished wells in a polyethylene sheet using a Black and Decker Thermogrip glue gun adding a dab of glue in the well and pushing the discs down firmly. The discs can be reinforced with polypropylene or metal mesh. Typically, each patch bears 5 mg of beads, having 1 micromole of spacer arm linked Pepsyn-K. The top right hand corner of every plate is notched or drilled as a reference to prevent the plate being incorrectly aligned at any step.

EXAMPLE 3

A Preparation of A Polymeric "Film" Plate:

A 10 mm thick plate of linear high density polyethylene is floated in a water bath at 70° C. and treated with 5M chromium trioxide in 5.3M sulfuric acid for two hours. The plate is washed with water many times, then with methanol, and then with ether, and dried under vacuum. The surface bound carboxylic acids are converted to acid chlorides by treatment with 20% thionyl chloride in chloroform for two hours. The plate is rapidly washed with chloroform, then ether, and dried under a stream of nitrogen and used immediately. This acid chloride functionalized plate can be derivatized by a variety of reagents to introduce many functionalities. Linear polymers, such as polyethylenimine, poly(amino)functionalized polyethylene glycols, and saccharide may be added to the plates by conventional chemistries. For example, for introduction of acryloyl groups, the plate may be treated with either a solution of N-(3-aminopropyl) methacrylamide hydrochloride and triethylamine in DMF, or it may be treated with neat (undiluted) diaminopropane for two hours, followed by washing thoroughly with water, then methanol, then ether, and then treated with a solution of acryloyl chloride and disopropylethyl amine in THF. The plate is washed well consecutively with methanol and ether, and dried under vacuum. The plate is now ready for grafting or casting of a gel film thereon as the substrate in the specific address areas.

The gels which may be cast into the wells of the substrate plate or grafted to the acryloyl groups on the surface of a film plate can have a variety of concentrations, cross-linking levels, functional linkers and amino linker loading. To prepare a typical gel, under nitrogen, a 5 ml portion of deoxygenated water (under vacuum for 20 minutes) is added to 18.5 mg of bisacryloyldiaminohexane, 295 mg of dimethylacrylamide, and 186 mg of the monoacrylamide of 1,6 diaminohexane hydrochloride. This is filtered onto 15 mg of ammonium persulfate and treated with 30 uL of pH 6 TEMED solution in water. In a glove bag under nitrogen, the monomer solution is rapidly transferred to each well of the plate. The plate is sealed in a plastic bag with an open beaker of deoxygenated water and allowed to gel. After curing over night the plate is washed with water and soaked in 1N sodium hydroxide for 2 hours. Two water washes of 15 minutes each followed by at least four washes in DMF give a plate which is ready for peptide synthesis.

EXAMPLE 4

Spacer Arm Derivatization of The Film:

Optionally a gel film plate of the type in Example 3 may have a tetrapeptide spacer attached to the substrate. A plate prepared as in Example 3 had Fmoc-beta-alanine (BAla) coupled to it (standard PyBOP+HOBt/NMM procedure, 2 hours). Following thorough DMF washes, the plate was treated with 30% piperidine in DMF (1, 45 minutes). The plate was washed 2 times with DMF, and the piperidine treatments and subsequent washes were pooled and read spectrophotometrically at 301 nm to determine the Fmoc-loading (in this example 2 micromoles per substrate area). Three more coupling cycles were then performed adding Fmoc-epsilon-aminocaproic acid twice, then beta-alanine again to give the final BAla-Aca-BAla spacer arm film plate as used in the preferred embodiment for ASBCL or ASPCL libraries.

EXAMPLE 5

Construction of A 10×10 Hexapeptide ASPCL Plate:

The method of this invention allows the construction of arrays of sequences at any 2 sequence positions within peptides of any reasonable size with several positions being incorporated as mixtures. The preferred embodiment of the method is to prepare hexapeptides with the central 2 AA's arrayed, the other 4 positions redundantly mixed, and the final sequence AA is N-acetylated. For film plates it is preferred to add a spacer arm peptide to the film prior to construction of the library, and with beaded plates an octapeptide spacer is attached prior to embedding in the glue. The following sequence of operations is followed to prepare a Hexapeptide ASPCL with a known central (3,4) AA sequence:

i) Apply an edge gasket and a border-frame spacer on the substrate plate (see FIG. 5) to make a flat "dish" type reactor. As an alternative to use of the screwed pin base plate assembly of FIG. 1, one may use standard large office clips, or wing nuts and standard bolts and washers to hold the parts together;

ii) Wash with DMF 2× using horizontal action shaker;

iii) Couple 10 mL preactivated MIX solution made as per Example 1 for 2 hours, while covering plate with foil tent;

iv) Wash with DMF 3×;

v) Deblock with 30% piperidine in DMF 1 min, 10 min;

vi) Wash with DMF 5×;

vii) Repeat steps iii) to vi);

viii) Dismount edge gasket and frame spacer, and mount slotted block assembly with 100 hole gasket to base plate as in FIG. 1 with slots in a first, horizontal orientation (L TO R when facing the assembly). DMF solvent is placed in alternate wells and the dry wells observed carefully to ensure no leakage. Prepare in vials the following amino acids: 1. Fmoc-L-Nle-OH 0.14 g; 2. Fmoc-L-His(Trt)-OH 0.25 g; 3. Fmoc-L-Pro-OH 0.135 g; 4. Fmoc-L-Gln(Trt)-OH 0.244 g; 5. Fmoc-Tyr(tBu)OH 0.183 g, 6. Fmoc-Gly-OH 0.116 g; 7. Fmoc-L-Phe-OH 0.154 g; 8. Fmoc-L-Arg(Pmc)-OH 0.265 g; 9. Fmoc-L-Glu(OtBu)-OH 0.17 g; 10. Fmoc- D-Ala-OH 0.124 g. To each of these vials add and mix PyBOP 0.27 g and HOBt 0.06 g, and 2 mL of 0.3M N-methylmorpholine in DMF. Add each to a designated horizontal slot: 1 to top slot; 2 to next slot, etc.;

ix) Maintain at room temperature for 2 hours to complete coupling;

x) Disassemble and remount with edge-gasket and border-frame spacer;

xi) Wash with DMF 3×;

xii) Deprotect with 30% piperidine in DMF 1 minute, 10 minutes;

xiii) Wash with DMF 5×;

xiv) Mount slot block with slots rotated 90°, i.e., in a vertical orientation, and repeat coupling as described in viii) except 1 is coupled to the left hand slot, 2 to the next slot, etc.;

xv) Disassemble and remount with edge-gasket and border-frame spacer;

xvi) Remove Fmoc group and perform 2 cycles of mixture incorporation as described in i) to vii);

xvii) Remove Fmoc-group and wash with DMF 5×;

xviii) Acetylate with 0.3M acetic anhydride +0.3M HOBt in DMF (10 mL) for 1 hour;

xix) Wash DMF 5×, Methanol 5×;

xx) Treat with 95:5 TFA/water for 2 hours;

xxi) Wash Methanol 5×, aqueous buffer 5×. Store in sealed bag at 4 degrees prior to probing to screen a target.

Numbering from the carboxy terminus, the resulting hexapeptides are characterized as XX-$A_4$, $A_3$-XX with the $A_3$ and $A_4$ known sequence being uniquely addressable. That is, the central dipeptide is known from its unique address by use of the slotted block, the hexapeptide at address 001 being XX-D-Ala-L-Nle-XX, at address 002 being XX-L-Glu-L-Nle-XX, etc., to address 100 being XX-L-Nle-D-Ala-XX.

EXAMPLE 6

Construction of A 10×10 Hexapeptide ASPCL on a Gel Film Plate

Instead of a bead plate, a gel film plate as in Examples 3 and 4 may be similarly employed to construct an ASPCL library by the process of Example 5. This gel film ASPCL is used to screen, see Example 6 below.

EXAMPLE 7

Determination of Binding Elements in the Interaction of Streptavidin with Peptides A film library plate of Examples 3 and 4 was constructed similarly to Example 6 with the selection of 10 amino acids as indicated. $^{125}I$ labelled streptavidin was prepared and purified by standard procedures; a fluorescently labelled form was also prepared by reaction of AMCA-NHS (Pierce) with the protein, excess reagent being removed by dialysis. Firstly, the iodinated protein was incubated with the plate overnight in a phosphate buffer containing 150 mM salt, Tween detergent and bovine serum albumin (1 mg/mL). The plate was washed with the buffer 3 times, placed on a standard laboratory X-ray film with an enhancer plate and exposed overnight. The developed film shows strong affinity in specific address locations corresponding to 2 central dipeptides HP and RR. The plate was then washed repeatedly with 6M guanidine hydrochloride, and buffer medium, then reincubated with the fluorescent AMCA-streptavidin overnight. After washing the plate was irradiated with long wave length uv light and visible confirmation obtained of the previously deduced binding elements. Subsequent iterations as described above further defines the active dipeptides at each end for complete hexapeptide characterization.

It should be understood that various modifications within the scope of this invention can be made by one of ordinary skill in the art without departing from the spirit thereof. We therefore wish our invention to be defined by the scope of the appended claims in view of the specification as broadly as the prior art will permit.

SEQUENCE LISTING ( 1 ) GENERAL INFORMATION:

( i i i ) NUMBER OF SEQUENCES: 101

( 2 ) INFORMATION FOR SEQ ID NO: 1:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Addresses 1.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu refers to Nle (or normal-leucine) and Ala refers to
Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 1: 1 to 6

(xi) SEQUENCE DESCRIPTION: SEQ ID NO: 1:

Xaa   Xaa   Leu   Ala   Xaa   Xaa
1                                    5

(2) INFORMATION FOR SEQ ID NO: 2:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for
            Streptavidin Test, Address 2.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 2: 1 to 6

(xi) SEQUENCE DESCRIPTION: SEQ ID NO: 2:

Xaa   Xaa   Leu   Glu   Xaa   Xaa
1                                    5

(2) INFORMATION FOR SEQ ID NO: 3:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for

Streptavidin Test, Address 3.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 3: 1 to 6

( x i ) SEQUENCE DESCRIPTION: SEQ ID NO: 3:

Xaa   Xaa   Leu   Arg   Xaa   Xaa
1                       5

( 2 ) INFORMATION FOR SEQ ID NO: 4:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 4.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 4: 1 to 6

( x i ) SEQUENCE DESCRIPTION: SEQ ID NO: 4:

Xaa   Xaa   Leu   Phe   Xaa   Xaa
1                       5

( 2 ) INFORMATION FOR SEQ ID NO: 5:

( i ) SEQUENCE CHARACTERISTICS:

( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 5.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 5: 1 to 6

( x i ) SEQUENCE DESCRIPTION: SEQ ID NO: 5:

Xaa   Xaa   Leu   Gly   Xaa   Xaa
1                       5

( 2 ) INFORMATION FOR SEQ ID NO: 6:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 6.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 6: 1 to 6

( x i ) SEQUENCE DESCRIPTION: SEQ ID NO: 6:

Xaa  Xaa  Leu  Tyr  Xaa  Xaa
1                   5

( 2 ) INFORMATION FOR SEQ ID NO: 7:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 × 10 Array Sequence Ligands for
          Streptavidin Test, Address 7.
    ( B ) LOCATION:
    ( C ) IDENTIFICATION METHOD: Constructed using an
          Arris Pharmaceutical PILOT Support Array System
    ( D ) OTHER INFORMATION: Biological activity unknown.
          Xaa represents a random amino acid selected from
          mixtures of the following 10 amino acids to give
          equal incorporation: Nle, His, Pro, Gln, Tyr, Gly,
          Phe, Arg, Glu, Ala. Where Leu or Ala is
          specified at any position in the sequence, then Leu
          refers to Nle (or normal-leucine) and Ala refers to
          Ala (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 7: 1 to 6

( x i ) SEQUENCE DESCRIPTION: SEQ ID NO: 7:

Xaa  Xaa  Leu  Gln  Xaa  Xaa
1                   5

( 2 ) INFORMATION FOR SEQ ID NO: 8:

( i ) SEQUENCE CHARACTERISTICS:
    ( A ) LENGTH: 6
    ( B ) TYPE: Amino Acids
    ( C ) STRANDEDNESS:
    ( D ) TOPOLOGY: Linear ( i i ) MOLECULE TYPE: Peptide
    ( A ) DESCRIPTION:

( i x ) FEATURE:
    ( A ) NAME/KEY: 10 × 10 Array Sequence Ligands for
          Streptavidin Test, Address 8.
    ( B ) LOCATION:
    ( C ) IDENTIFICATION METHOD: Constructed using an
          Arris Pharmaceutical PILOT Support Array System
    ( D ) OTHER INFORMATION: Biological activity unknown.
          Xaa represents a random amino acid selected from
          mixtures of the following 10 amino acids to give
          equal incorporation: Nle, His, Pro, Gln, Tyr, Gly,
          Phe, Arg, Glu, Ala. Where Leu or Ala is
          specified at any position in the sequence, then Leu
          refers to Nle (or normal-leucine) and Ala refers to
          Ala (or beta- alanine).

( x ) PUBLICATION INFORMATION:
    ( A ) AUTHORS:
    ( B ) TITLE:

```
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 8: 1 to 6

( x i ) SEQUENCE DESCRIPTION: SEQ ID NO: 8:

Xaa    Xaa    Leu    Pro    Xaa    Xaa
1                          5

( 2 ) INFORMATION FOR SEQ ID NO: 9:

( i ) SEQUENCE CHARACTERISTICS:
              ( A ) LENGTH: 6
              ( B ) TYPE: Amino Acids
              ( C ) STRANDEDNESS:
              ( D ) TOPOLOGY: Linear ( i i ) MOLECULE TYPE: Peptide
              ( A ) DESCRIPTION:

( i x ) FEATURE:
              ( A ) NAME/KEY: 10 × 10 Array Sequence Ligands for
                    Streptavidin Test, Address 9.
              ( B ) LOCATION:
              ( C ) IDENTIFICATION METHOD: Constructed using an
                    Arris Pharmaceutical PILOT Support Array System
              ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, Ala. Where Leu or Ala is
                    specified at any position in the sequence, then Leu
                    refers to Nle (or normal-leucine) and Ala refers to
                    Ala (or beta- alanine).

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO: 9: 1 to 6

( x i ) SEQUENCE DESCRIPTION: SEQ ID NO: 9:

Xaa    Xaa    Leu    His    Xaa    Xaa
1                          5

( 2 ) INFORMATION FOR SEQ ID NO: 10:

( i ) SEQUENCE CHARACTERISTICS:
              ( A ) LENGTH: 6
              ( B ) TYPE: Amino Acids
              ( C ) STRANDEDNESS:
              ( D ) TOPOLOGY: Linear ( i i ) MOLECULE TYPE: Peptide
              ( A ) DESCRIPTION:

( i x ) FEATURE:
              ( A ) NAME/KEY: 10 × 10 Array Sequence Ligands for
                    Streptavidin Test, Address 10.
              ( B ) LOCATION:
              ( C ) IDENTIFICATION METHOD: Constructed using an
                    Arris Pharmaceutical PILOT Support Array System
              ( D ) OTHER INFORMATION: Biological activity unknown.
                    Xaa represents a random amino acid selected from
``` mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 10: 1 to 6

( x i ) SEQUENCE DESCRIPTION: SEQ ID NO: 10:

Xaa    Xaa    Leu    Leu    Xaa    Xaa
1                                                  5

( 2 ) INFORMATION FOR SEQ ID NO: 11:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 11.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 11: 1 to 6

( x i ) SEQUENCE DESCRIPTION: SEQ ID NO: 11:

Xaa    Xaa    His    Ala    Xaa    Xaa
1                                                  5

( 2 ) INFORMATION FOR SEQ ID NO: 12:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide (A) DESCRIPTION:

(ix) FEATURE:
    (A) NAME/KEY: 10 × 10 Array Sequence Ligands for Streptavidin Test, Address 12.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 12: 1 to 6

(xi) SEQUENCE DESCRIPTION: SEQ ID NO: 12:

```
Xaa   Xaa   His   Glu   Xaa   Xaa
1                       5
```

(2) INFORMATION FOR SEQ ID NO: 13:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for Streptavidin Test, Address 13.
    (B) LOCATION:
    (C) IDENTIFICATION METHOD: Constructed using an Arris Pharmaceutical PILOT Support Array System
    (D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 13: 1 to 6

(xi) SEQUENCE DESCRIPTION: SEQ ID NO: 13:

```
Xaa   Xaa   His   Arg   Xaa   Xaa
1                       5
```

( 2 ) INFORMATION FOR SEQ ID NO: 14:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 14.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 14: 1 to 6

( x i ) SEQUENCE DESCRIPTION: SEQ ID NO: 14:

Xaa    Xaa    His    Phe    Xaa    Xaa
1                                          5

( 2 ) INFORMATION FOR SEQ ID NO: 15:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 15.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

(H) DOCUMENT NUMBER:
(I) FILING DATE:
(J) PUBLICATION DATE:
(K) RELEVANT RESIDUES IN SEQ ID NO: 15: 1 to 6

( x i ) SEQUENCE DESCRIPTION: SEQ ID NO: 15:

Xaa  Xaa  His  Gly  Xaa  Xaa
1                    5

( 2 ) INFORMATION FOR SEQ ID NO: 16:

( i ) SEQUENCE CHARACTERISTICS:
           ( A ) LENGTH: 6
           ( B ) TYPE: Amino Acids
           ( C ) STRANDEDNESS:
           ( D ) TOPOLOGY: Linear ( i i ) MOLECULE TYPE: Peptide
           ( A ) DESCRIPTION:

( i x ) FEATURE:
           ( A ) NAME/KEY: 10 × 10 Array Sequence Ligands for
                 Streptavidin Test, Address 16.
           ( B ) LOCATION:
           ( C ) IDENTIFICATION METHOD: Constructed using an
                 Arris Pharmaceutical PILOT Support Array System
           ( D ) OTHER INFORMATION: Biological activity unknown.
                 Xaa represents a random amino acid selected from
                 mixtures of the following 10 amino acids to give
                 equal incorporation: Nle, His, Pro, Gln, Tyr, Gly,
                 Phe, Arg, Glu, Ala. Where Leu or Ala is
                 specified at any position in the sequence, then Leu
                 refers to Nle (or normal-leucine) and Ala refers to
                 Ala (or beta- alanine).

( x ) PUBLICATION INFORMATION:
           ( A ) AUTHORS:
           ( B ) TITLE:
           ( C ) JOURNAL:
           ( D ) VOLUME:
           ( E ) ISSUE:
           ( F ) PAGES:
           ( G ) DATE:
           ( H ) DOCUMENT NUMBER:
           ( I ) FILING DATE:
           ( J ) PUBLICATION DATE:
           ( K ) RELEVANT RESIDUES IN SEQ ID NO: 16: 1 to 6

( x i ) SEQUENCE DESCRIPTION: SEQ ID NO: 16:

Xaa  Xaa  His  Tyr  Xaa  Xaa
1                    5

( 2 ) INFORMATION FOR SEQ ID NO: 17:

( i ) SEQUENCE CHARACTERISTICS:
           ( A ) LENGTH: 6
           ( B ) TYPE: Amino Acids
           ( C ) STRANDEDNESS:
           ( D ) TOPOLOGY: Linear ( i i ) MOLECULE TYPE: Peptide
           ( A ) DESCRIPTION:

( i x ) FEATURE:
           ( A ) NAME/KEY: 10 × 10 Array Sequence Ligands for
                 Streptavidin Test, Address 17.
           ( B ) LOCATION:
           ( C ) IDENTIFICATION METHOD: Constructed using an
                 Arris Pharmaceutical PILOT Support Array System
           ( D ) OTHER INFORMATION: Biological activity unknown.
                 Xaa represents a random amino acid selected from
                 mixtures of the following 10 amino acids to give
                 equal incorporation: Nle, His, Pro, Gln, Tyr, Gly,
                 Phe, Arg, Glu, Ala. Where Leu or Ala is
                 specified at any position in the sequence, then Leu
                 refers to Nle (or normal-leucine) and Ala refers to Ala (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 17: 1 to 6

( x i ) SEQUENCE DESCRIPTION: SEQ ID NO: 17:

```
Xaa   Xaa   His   Gln   Xaa   Xaa
1                       5
```

( 2 ) INFORMATION FOR SEQ ID NO: 18:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 18.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 18: 1 to 6

( x i ) SEQUENCE DESCRIPTION: SEQ ID NO: 18:

```
Xaa   Xaa   His   Pro   Xaa   Xaa
1                       5
```

( 2 ) INFORMATION FOR SEQ ID NO: 19:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 19.

( B ) LOCATION:
( C ) IDENTIFICATION METHOD: Constructed using an
    Arris Pharmaceutical PILOT Support Array System
( D ) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, Ala. Where Leu or Ala is
    specified at any position in the sequence, then Leu
    refers to Nle (or normal-leucine) and Ala refers to
    Ala (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 19: 1 to 6

( x i ) SEQUENCE DESCRIPTION: SEQ ID NO: 19:

Xaa    Xaa    His    His    Xaa    Xaa
1                          5

( 2 ) INFORMATION FOR SEQ ID NO: 20:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 20.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 20: 1 to 6

( x i ) SEQUENCE DESCRIPTION: SEQ ID NO: 20:

Xaa    Xaa    His    Leu    Xaa    Xaa
1                          5

( 2 ) INFORMATION FOR SEQ ID NO: 21:

( i ) SEQUENCE CHARACTERISTICS:
        ( A ) LENGTH: 6

(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 × 10 Array Sequence Ligands for Streptavidin Test, Address 21.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 21: 1 to 6

(xi) SEQUENCE DESCRIPTION: SEQ ID NO: 21:

Xaa  Xaa  Pro  Ala  Xaa  Xaa
1                  5

(2) INFORMATION FOR SEQ ID NO: 22:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 × 10 Array Sequence Ligands for Streptavidin Test, Address 22.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 22: 1 to 6

( x i ) SEQUENCE DESCRIPTION: SEQ ID NO: 22:

Xaa Xaa Pro Glu Xaa Xaa
1              5

(2) INFORMATION FOR SEQ ID NO: 23:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 23.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 23: 1 to 6

( x i ) SEQUENCE DESCRIPTION: SEQ ID NO: 23:

Xaa Xaa Pro Arg Xaa Xaa
1              5

(2) INFORMATION FOR SEQ ID NO: 24:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 24.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 24: 1 to 6

(xi) SEQUENCE DESCRIPTION: SEQ ID NO: 24:

Xaa Xaa Pro Phe Xaa Xaa
1               5

(2) INFORMATION FOR SEQ ID NO: 25:

(i) SEQUENCE CHARACTERISTICS:
      (A) LENGTH: 6
      (B) TYPE: Amino Acids
      (C) STRANDEDNESS:
      (D) TOPOLOGY: Linear (ii) MOLECULE TYPE: Peptide
      (A) DESCRIPTION:

(ix) FEATURE:
      (A) NAME/KEY: 10 × 10 Array Sequence Ligands for
          Streptavidin Test, Address 25.
      (B) LOCATION:
      (C) IDENTIFICATION METHOD: Constructed using an
          Arris Pharmaceutical PILOT Support Array System
      (D) OTHER INFORMATION: Biological activity unknown.
          Xaa represents a random amino acid selected from
          mixtures of the following 10 amino acids to give
          equal incorporation: Nle, His, Pro, Gln, Tyr, Gly,
          Phe, Arg, Glu, Ala. Where Leu or Ala is
          specified at any position in the sequence, then Leu
          refers to Nle (or normal-leucine) and Ala refers to
          Ala (or beta- alanine).

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO: 25: 1 to 6

(xi) SEQUENCE DESCRIPTION: SEQ ID NO: 25:

Xaa Xaa Pro Gly Xaa Xaa
1               5

(2) INFORMATION FOR SEQ ID NO: 26:

(i) SEQUENCE CHARACTERISTICS:
      (A) LENGTH: 6
      (B) TYPE: Amino Acids
      (C) STRANDEDNESS:
      (D) TOPOLOGY: Linear (ii) MOLECULE TYPE: Peptide
      (A) DESCRIPTION:

(ix) FEATURE:
      (A) NAME/KEY: 10 × 10 Array Sequence Ligands for
          Streptavidin Test, Address 26.
      (B) LOCATION:
      (C) IDENTIFICATION METHOD: Constructed using an
          Arris Pharmaceutical PILOT Support Array System
      (D) OTHER INFORMATION: Biological activity unknown.
          Xaa represents a random amino acid selected from mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 26: 1 to 6

( x i ) SEQUENCE DESCRIPTION: SEQ ID NO: 26:

Xaa    Xaa    Pro    Tyr    Xaa    Xaa
1                                        5

( 2 ) INFORMATION FOR SEQ ID NO: 27:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 27.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 27: 1 to 6

( x i ) SEQUENCE DESCRIPTION: SEQ ID NO: 27:

Xaa    Xaa    Pro    Gln    Xaa    Xaa
1                                        5

( 2 ) INFORMATION FOR SEQ ID NO: 28:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide (A) DESCRIPTION:

(ix) FEATURE:
    (A) NAME/KEY: 10 × 10 Array Sequence Ligands for
        Streptavidin Test, Address 28.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, Ala. Where Leu or Ala is
        specified at any position in the sequence, then Leu
        refers to Nle (or normal-leucine) and Ala refers to
        Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 28: 1 to 6

(xi) SEQUENCE DESCRIPTION: SEQ ID NO: 28:

Xaa    Xaa    Pro    Pro    Xaa    Xaa
1                                    5

(2) INFORMATION FOR SEQ ID NO: 29:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for
            Streptavidin Test, Address 29.
        (B) LOCATION:
        (C) IDENTIFICATION METHOD: Constructed using an
            Arris Pharmaceutical PILOT Support Array System
        (D) OTHER INFORMATION: Exhibits specific binding
            activity with streptavidin. Xaa represents a
            random amino acid selected from mixtures of the
            following 10 amino acids to give equal
            incorporation: Nle, His, Pro, Gln, Tyr, Gly, Phe,
            Arg, Glu, Ala. Where Leu or Ala is specified at
            any position in the sequence, then Leu refers to
            Nle (or normal-leucine) and Ala refers to Ala (or
            beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 29: 1 to 6

(xi) SEQUENCE DESCRIPTION: SEQ ID NO: 29:

Xaa    Xaa    Pro    His    Xaa    Xaa
1                                    5

( 2 ) INFORMATION FOR SEQ ID NO: 30:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 30.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 30: 1 to 6

( x i ) SEQUENCE DESCRIPTION: SEQ ID NO: 30:

Xaa    Xaa    Pro    Leu    Xaa    Xaa
1                                       5

( 2 ) INFORMATION FOR SEQ ID NO: 31:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 31.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

5,591,646

49

-continued ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 31: 1 to 6

( x i ) SEQUENCE DESCRIPTION: SEQ ID NO: 31:

Xaa    Xaa    Gln    Ala    Xaa    Xaa
1                           5

( 2 ) INFORMATION FOR SEQ ID NO: 32:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 32.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to
                        Ala (or beta- alanine).

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 32: 1 to 6

( x i ) SEQUENCE DESCRIPTION: SEQ ID NO: 32:

Xaa    Xaa    Gln    Glu    Xaa    Xaa
1                           5

( 2 ) INFORMATION FOR SEQ ID NO: 33:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 33.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu refers to Nle (or normal-leucine) and Ala refers to
Ala (or beta-alanine).

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO: 33: 1 to 6

( x i ) SEQUENCE DESCRIPTION: SEQ ID NO: 33:

Xaa   Xaa   Gln   Arg   Xaa   Xaa
1                                      5

( 2 ) INFORMATION FOR SEQ ID NO: 34:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 34.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta-alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 34: 1 to 6

( x i ) SEQUENCE DESCRIPTION: SEQ ID NO: 34:

Xaa   Xaa   Gln   Phe   Xaa   Xaa
1                                      5

( 2 ) INFORMATION FOR SEQ ID NO: 35:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for

Streptavidin Test, Address 35.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 35: 1 to 6

( x i ) SEQUENCE DESCRIPTION: SEQ ID NO: 35:

Xaa    Xaa    Gln    Gly    Xaa    Xaa
1                          5

( 2 ) INFORMATION FOR SEQ ID NO: 36:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 36.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 36: 1 to 6

( x i ) SEQUENCE DESCRIPTION: SEQ ID NO: 36:

Xaa    Xaa    Gln    Tyr    Xaa    Xaa
1                          5

( 2 ) INFORMATION FOR SEQ ID NO: 37:

( i ) SEQUENCE CHARACTERISTICS:

( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 37.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 37: 1 to 6

( x i ) SEQUENCE DESCRIPTION: SEQ ID NO: 37:

Xaa  Xaa  Gln  Gln  Xaa  Xaa
1                       5

( 2 ) INFORMATION FOR SEQ ID NO: 38:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 38.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 38: 1 to 6

( x i ) SEQUENCE DESCRIPTION: SEQ ID NO: 38:

Xaa Xaa Gln Pro Xaa Xaa
1                  5

( 2 ) INFORMATION FOR SEQ ID NO: 39:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 39.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 39: 1 to 6

( x i ) SEQUENCE DESCRIPTION: SEQ ID NO: 39:

Xaa Xaa Gln His Xaa Xaa
1                  5

( 2 ) INFORMATION FOR SEQ ID NO: 40:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 40.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:

(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 40: 1 to 6

( x i ) SEQUENCE DESCRIPTION: SEQ ID NO: 40:

Xaa   Xaa   Gln   Leu   Xaa   Xaa
1                       5

( 2 ) INFORMATION FOR SEQ ID NO: 41:

( i ) SEQUENCE CHARACTERISTICS:
(A) LENGTH: 6
(B) TYPE: Amino Acids
(C) STRANDEDNESS:
(D) TOPOLOGY: Linear ( i i ) MOLECULE TYPE: Peptide
(A) DESCRIPTION:

( i x ) FEATURE:
(A) NAME/KEY: 10 × 10 Array Sequence Ligands for
Streptavidin Test, Address 41.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 41: 1 to 6

( x i ) SEQUENCE DESCRIPTION: SEQ ID NO: 41:

Xaa   Xaa   Tyr   Ala   Xaa   Xaa
1                       5

( 2 ) INFORMATION FOR SEQ ID NO: 42:

( i ) SEQUENCE CHARACTERISTICS:
(A) LENGTH: 6
(B) TYPE: Amino Acids
(C) STRANDEDNESS:
(D) TOPOLOGY: Linear ( i i ) MOLECULE TYPE: Peptide
(A) DESCRIPTION:

( i x ) FEATURE:
(A) NAME/KEY: 10 × 10 Array Sequence Ligands for
Streptavidin Test, Address 42.
(B) LOCATION:
(C) IDENTIFICATION METHOD: Constructed using an
Arris Pharmaceutical PILOT Support Array System
(D) OTHER INFORMATION: Biological activity unknown.

Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 42: 1 to 6

( x i ) SEQUENCE DESCRIPTION: SEQ ID NO: 42:

Xaa    Xaa    Tyr    Glu    Xaa    Xaa
1                                                       5

( 2 ) INFORMATION FOR SEQ ID NO: 43:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 43.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 43: 1 to 6

( x i ) SEQUENCE DESCRIPTION: SEQ ID NO: 43:

Xaa    Xaa    Tyr    Arg    Xaa    Xaa
1                                                       5

( 2 ) INFORMATION FOR SEQ ID NO: 44:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
       ( A ) DESCRIPTION:

( i x ) FEATURE:
       ( A ) NAME/KEY: 10 × 10 Array Sequence Ligands for
            Streptavidin Test, Address 44.
       ( B ) LOCATION:
       ( C ) IDENTIFICATION METHOD: Constructed using an
            Arris Pharmaceutical PILOT Support Array System
       ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
       ( A ) AUTHORS:
       ( B ) TITLE:
       ( C ) JOURNAL:
       ( D ) VOLUME:
       ( E ) ISSUE:
       ( F ) PAGES:
       ( G ) DATE:
       ( H ) DOCUMENT NUMBER:
       ( I ) FILING DATE:
       ( J ) PUBLICATION DATE:
       ( K ) RELEVANT RESIDUES IN SEQ ID NO: 44: 1 to 6

( x i ) SEQUENCE DESCRIPTION: SEQ ID NO: 44:

```
Xaa   Xaa   Tyr   Phe   Xaa   Xaa
1                       5
```

( 2 ) INFORMATION FOR SEQ ID NO: 45:

( i ) SEQUENCE CHARACTERISTICS:
       ( A ) LENGTH: 6
       ( B ) TYPE: Amino Acids
       ( C ) STRANDEDNESS:
       ( D ) TOPOLOGY: Linear ( i i ) MOLECULE TYPE: Peptide
       ( A ) DESCRIPTION:

( i x ) FEATURE:
       ( A ) NAME/KEY: 10 × 10 Array Sequence Ligands for
            Streptavidin Test, Address 45.
       ( B ) LOCATION:
       ( C ) IDENTIFICATION METHOD: Constructed using an
            Arris Pharmaceutical PILOT Support Array System
       ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
       ( A ) AUTHORS:
       ( B ) TITLE:
       ( C ) JOURNAL:
       ( D ) VOLUME:
       ( E ) ISSUE:
       ( F ) PAGES:
       ( G ) DATE:
       ( H ) DOCUMENT NUMBER:
       ( I ) FILING DATE:
       ( J ) PUBLICATION DATE:
       ( K ) RELEVANT RESIDUES IN SEQ ID NO: 45: 1 to 6

( x i ) SEQUENCE DESCRIPTION: SEQ ID NO: 45:

```
Xaa   Xaa   Tyr   Gly   Xaa   Xaa
1                       5
```

( 2 ) INFORMATION FOR SEQ ID NO: 46:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 46.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 46: 1 to 6

( x i ) SEQUENCE DESCRIPTION: SEQ ID NO: 46:

Xaa    Xaa    Tyr    Tyr    Xaa    Xaa
1                                         5

( 2 ) INFORMATION FOR SEQ ID NO: 47:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 47.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 47: 1 to 6

( x i ) SEQUENCE DESCRIPTION: SEQ ID NO: 47:

Xaa    Xaa    Tyr    Gln    Xaa    Xaa
1                                 5

( 2 ) INFORMATION FOR SEQ ID NO: 48:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 × 10 Array Sequence Ligands for
                            Streptavidin Test, Address 48.
                    ( B ) LOCATION:
                    ( C ) IDENTIFICATION METHOD: Constructed using an
                            Arris Pharmaceutical PILOT Support Array System
                    ( D ) OTHER INFORMATION: Biological activity unknown.
                            Xaa represents a random amino acid selected from
                            mixtures of the following 10 amino acids to give
                            equal incorporation: Nle, His, Pro, Gln, Tyr, Gly,
                            Phe, Arg, Glu, Ala. Where Leu or Ala is
                            specified at any position in the sequence, then Leu
                            refers to Nle (or normal-leucine) and Ala refers to
                            Ala (or beta- alanine).

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO: 48: 1 to 6

( x i ) SEQUENCE DESCRIPTION: SEQ ID NO: 48:

Xaa    Xaa    Tyr    Pro    Xaa    Xaa
1                                 5

( 2 ) INFORMATION FOR SEQ ID NO: 49:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 × 10 Array Sequence Ligands for
                            Streptavidin Test, Address 49.
                    ( B ) LOCATION:
                    ( C ) IDENTIFICATION METHOD: Constructed using an
                            Arris Pharmaceutical PILOT Support Array System
                    ( D ) OTHER INFORMATION: Biological activity unknown.
                            Xaa represents a random amino acid selected from
                            mixtures of the following 10 amino acids to give
                            equal incorporation: Nle, His, Pro, Gln, Tyr, Gly,
                            Phe, Arg, Glu, Ala. Where Leu or Ala is
                            specified at any position in the sequence, then Leu refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 49: 1 to 6

( x i ) SEQUENCE DESCRIPTION: SEQ ID NO: 49:

Xaa  Xaa  Tyr  His  Xaa  Xaa
1                     5

( 2 ) INFORMATION FOR SEQ ID NO: 50:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 50.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 50: 1 to 6

( x i ) SEQUENCE DESCRIPTION: SEQ ID NO: 50:

Xaa  Xaa  Tyr  Leu  Xaa  Xaa
1                     5

( 2 ) INFORMATION FOR SEQ ID NO: 51:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for

Streptavidin Test, Address 51.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 51: 1 to 6

(xi) SEQUENCE DESCRIPTION: SEQ ID NO: 51:

Xaa  Xaa  Gly  Ala  Xaa  Xaa
1                    5

(2) INFORMATION FOR SEQ ID NO: 52:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 × 10 Array Sequence Ligands for
Streptavidin Test, Address 52.
(B) LOCATION:
(C) IDENTIFICATION METHOD: Constructed using an
Arris Pharmaceutical PILOT Support Array System
(D) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 52: 1 to 6

(xi) SEQUENCE DESCRIPTION: SEQ ID NO: 52:

Xaa  Xaa  Gly  Glu  Xaa  Xaa
1                    5

(2) INFORMATION FOR SEQ ID NO: 53:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for
        Streptavidin Test, Address 53.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, Ala. Where Leu or Ala is
        specified at any position in the sequence, then Leu
        refers to Nle (or normal-leucine) and Ala refers to
        Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 53: 1 to 6

(xi) SEQUENCE DESCRIPTION: SEQ ID NO: 53:

Xaa   Xaa   Gly   Arg   Xaa   Xaa
1                       5

(2) INFORMATION FOR SEQ ID NO: 54:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for
            Streptavidin Test, Address 54.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:

( K ) RELEVANT RESIDUES IN SEQ ID NO: 54: 1 to 6

( x i ) SEQUENCE DESCRIPTION: SEQ ID NO: 54:

Xaa   Xaa   Gly   Phe   Xaa   Xaa
1                       5

( 2 ) INFORMATION FOR SEQ ID NO: 55:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 55.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 55: 1 to 6

( x i ) SEQUENCE DESCRIPTION: SEQ ID NO: 55:

Xaa   Xaa   Gly   Gly   Xaa   Xaa
1                       5

( 2 ) INFORMATION FOR SEQ ID NO: 56:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 56.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:

(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 56: 1 to 6

(xi) SEQUENCE DESCRIPTION: SEQ ID NO: 56:

Xaa  Xaa  Gly  Tyr  Xaa  Xaa
1                   5

(2) INFORMATION FOR SEQ ID NO: 57:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for
        Streptavidin Test, Address 57.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, Ala. Where Leu or Ala is
        specified at any position in the sequence, then Leu
        refers to Nle (or normal-leucine) and Ala refers to
        Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 57: 1 to 6

(xi) SEQUENCE DESCRIPTION: SEQ ID NO: 57:

Xaa  Xaa  Gly  Gln  Xaa  Xaa
1                   5

(2) INFORMATION FOR SEQ ID NO: 58:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for
        Streptavidin Test, Address 58.
    (B) LOCATION:
    (C) IDENTIFICATION METHOD: Constructed using an
        Arris Pharmaceutical PILOT Support Array System ( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 58: 1 to 6

( x i ) SEQUENCE DESCRIPTION: SEQ ID NO: 58:

Xaa    Xaa    Gly    Pro    Xaa    Xaa
1                                  5

( 2 ) INFORMATION FOR SEQ ID NO: 59:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 59.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 59: 1 to 6

( x i ) SEQUENCE DESCRIPTION: SEQ ID NO: 59:

Xaa    Xaa    Gly    His    Xaa    Xaa
1                                  5

( 2 ) INFORMATION FOR SEQ ID NO: 60:

( i ) SEQUENCE CHARACTERISTICS:
( A ) LENGTH: 6
( B ) TYPE: Amino Acids
( C ) STRANDEDNESS:
( D ) TOPOLOGY: Linear (i i) MOLECULE TYPE: Peptide
        (A) DESCRIPTION:

(i x) FEATURE:
        (A) NAME/KEY: 10 × 10 Array Sequence Ligands for
             Streptavidin Test, Address 60.
        (B) LOCATION:
        (C) IDENTIFICATION METHOD: Constructed using an
             Arris Pharmaceutical PILOT Support Array System
        (D) OTHER INFORMATION: Biological activity unknown.
             Xaa represents a random amino acid selected from
             mixtures of the following 10 amino acids to give
             equal incorporation: Nle, His, Pro, Gln, Tyr, Gly,
             Phe, Arg, Glu, Ala. Where Leu or Ala is
             specified at any position in the sequence, then Leu
             refers to Nle (or normal-leucine) and Ala refers to
             Ala (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 60: 1 to 6

(x i) SEQUENCE DESCRIPTION: SEQ ID NO: 60:

Xaa    Xaa    Gly    Leu    Xaa    Xaa
1                          5

(2) INFORMATION FOR SEQ ID NO: 61:

(i) SEQUENCE CHARACTERISTICS:
        (A) LENGTH: 6
        (B) TYPE: Amino Acids
        (C) STRANDEDNESS:
        (D) TOPOLOGY: Linear (i i) MOLECULE TYPE: Peptide
        (A) DESCRIPTION:

(i x) FEATURE:
        (A) NAME/KEY: 10 × 10 Array Sequence Ligands for
             Streptavidin Test, Address 61.
        (B) LOCATION:
        (C) IDENTIFICATION METHOD: Constructed using an
             Arris Pharmaceutical PILOT Support Array System
        (D) OTHER INFORMATION: Biological activity unknown.
             Xaa represents a random amino acid selected from
             mixtures of the following 10 amino acids to give
             equal incorporation: Nle, His, Pro, Gln, Tyr, Gly,
             Phe, Arg, Glu, Ala. Where Leu or Ala is
             specified at any position in the sequence, then Leu
             refers to Nle (or normal-leucine) and Ala refers to
             Ala (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 61: 1 to 6

(x i) SEQUENCE DESCRIPTION: SEQ ID NO: 61:

Xaa   Xaa   Phe   Ala   Xaa   Xaa
1                       5

( 2 ) INFORMATION FOR SEQ ID NO: 62:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 62.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 62: 1 to 6

( x i ) SEQUENCE DESCRIPTION: SEQ ID NO: 62:

Xaa   Xaa   Phe   Glu   Xaa   Xaa
1                       5

( 2 ) INFORMATION FOR SEQ ID NO: 63:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 63.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:

( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 63: 1 to 6

( x i ) SEQUENCE DESCRIPTION: SEQ ID NO: 63:

Xaa    Xaa    Phe    Arg    Xaa    Xaa
1                                  5

( 2 ) INFORMATION FOR SEQ ID NO: 64:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 64.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to
                        Ala (or beta- alanine).

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 64: 1 to 6

( x i ) SEQUENCE DESCRIPTION: SEQ ID NO: 64:

Xaa    Xaa    Phe    Phe    Xaa    Xaa
1                                  5

( 2 ) INFORMATION FOR SEQ ID NO: 65:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 65.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
   ( A ) AUTHORS:
   ( B ) TITLE:
   ( C ) JOURNAL:
   ( D ) VOLUME:
   ( E ) ISSUE:
   ( F ) PAGES:
   ( G ) DATE:
   ( H ) DOCUMENT NUMBER:
   ( I ) FILING DATE:
   ( J ) PUBLICATION DATE:
   ( K ) RELEVANT RESIDUES IN SEQ ID NO: 65: 1 to 6

( x i ) SEQUENCE DESCRIPTION: SEQ ID NO: 65:

Xaa    Xaa    Phe    Gly    Xaa    Xaa
1                          5

( 2 ) INFORMATION FOR SEQ ID NO: 66:

( i ) SEQUENCE CHARACTERISTICS:
      ( A ) LENGTH: 6
      ( B ) TYPE: Amino Acids
      ( C ) STRANDEDNESS:
      ( D ) TOPOLOGY: Linear ( i i ) MOLECULE TYPE: Peptide
      ( A ) DESCRIPTION:

( i x ) FEATURE:
      ( A ) NAME/KEY: 10 × 10 Array Sequence Ligands for
         Streptavidin Test, Address 66.
      ( B ) LOCATION:
      ( C ) IDENTIFICATION METHOD: Constructed using an
         Arris Pharmaceutical PILOT Support Array System
      ( D ) OTHER INFORMATION: Biological activity unknown.
         Xaa represents a random amino acid selected from
         mixtures of the following 10 amino acids to give
         equal incorporation: Nle, His, Pro, Gln, Tyr, Gly,
         Phe, Arg, Glu, Ala. Where Leu or Ala is
         specified at any position in the sequence, then Leu
         refers to Nle (or normal-leucine) and Ala refers to
         Ala (or beta- alanine).

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO: 66: 1 to 6

( x i ) SEQUENCE DESCRIPTION: SEQ ID NO: 66:

Xaa    Xaa    Phe    Tyr    Xaa    Xaa
1                          5

( 2 ) INFORMATION FOR SEQ ID NO: 67:

( i ) SEQUENCE CHARACTERISTICS:
      ( A ) LENGTH: 6
      ( B ) TYPE: Amino Acids
      ( C ) STRANDEDNESS:
      ( D ) TOPOLOGY: Linear ( i i ) MOLECULE TYPE: Peptide
      ( A ) DESCRIPTION:

( i x ) FEATURE:
  ( A ) NAME/KEY: 10 × 10 Array Sequence Ligands for
        Streptavidin Test, Address 67.
  ( B ) LOCATION:
  ( C ) IDENTIFICATION METHOD: Constructed using an
        Arris Pharmaceutical PILOT Support Array System
  ( D ) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, Ala. Where Leu or Ala is
        specified at any position in the sequence, then Leu
        refers to Nle (or normal-leucine) and Ala refers to
        Ala (or beta- alanine).

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO: 67: 1 to 6

( x i ) SEQUENCE DESCRIPTION: SEQ ID NO: 67:

Xaa    Xaa    Phe    Gln    Xaa    Xaa
1                          5

( 2 ) INFORMATION FOR SEQ ID NO: 68:

( i ) SEQUENCE CHARACTERISTICS:
      ( A ) LENGTH: 6
      ( B ) TYPE: Amino Acids
      ( C ) STRANDEDNESS:
      ( D ) TOPOLOGY: Linear ( i i ) MOLECULE TYPE: Peptide
      ( A ) DESCRIPTION:

( i x ) FEATURE:
      ( A ) NAME/KEY: 10 × 10 Array Sequence Ligands for
            Streptavidin Test, Address 68.
      ( B ) LOCATION:
      ( C ) IDENTIFICATION METHOD: Constructed using an
            Arris Pharmaceutical PILOT Support Array System
      ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO: 68: 1 to 6

( x i ) SEQUENCE DESCRIPTION: SEQ ID NO: 68:

Xaa    Xaa    Phe    Pro    Xaa    Xaa
1                          5

( 2 ) INFORMATION FOR SEQ ID NO: 69:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 69.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 69: 1 to 6

( x i ) SEQUENCE DESCRIPTION: SEQ ID NO: 69:

Xaa    Xaa    Phe    His    Xaa    Xaa
1                                        5

( 2 ) INFORMATION FOR SEQ ID NO: 70:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 70.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:

(I) FILING DATE:
(J) PUBLICATION DATE:
(K) RELEVANT RESIDUES IN SEQ ID NO: 70: 1 to 6

(xi) SEQUENCE DESCRIPTION: SEQ ID NO: 70:

Xaa Xaa Phe Leu Xaa Xaa
1             5

(2) INFORMATION FOR SEQ ID NO: 71:

(i) SEQUENCE CHARACTERISTICS:
     (A) LENGTH: 6
     (B) TYPE: Amino Acids
     (C) STRANDEDNESS:
     (D) TOPOLOGY: Linear (ii) MOLECULE TYPE: Peptide
     (A) DESCRIPTION:

(ix) FEATURE:
     (A) NAME/KEY: 10 × 10 Array Sequence Ligands for
         Streptavidin Test, Address 71.
     (B) LOCATION:
     (C) IDENTIFICATION METHOD: Constructed using an
         Arris Pharmaceutical PILOT Support Array System
     (D) OTHER INFORMATION: Biological activity unknown.
         Xaa represents a random amino acid selected from
         mixtures of the following 10 amino acids to give
         equal incorporation: Nle, His, Pro, Gln, Tyr, Gly,
         Phe, Arg, Glu, Ala. Where Leu or Ala is
         specified at any position in the sequence, then Leu
         refers to Nle (or normal-leucine) and Ala refers to
         Ala (or beta- alanine).

(x) PUBLICATION INFORMATION:
     (A) AUTHORS:
     (B) TITLE:
     (C) JOURNAL:
     (D) VOLUME:
     (E) ISSUE:
     (F) PAGES:
     (G) DATE:
     (H) DOCUMENT NUMBER:
     (I) FILING DATE:
     (J) PUBLICATION DATE:
     (K) RELEVANT RESIDUES IN SEQ ID NO: 71: 1 to 6

(xi) SEQUENCE DESCRIPTION: SEQ ID NO: 71:

Xaa Xaa Arg Ala Xaa Xaa
1             5

(2) INFORMATION FOR SEQ ID NO: 72:

(i) SEQUENCE CHARACTERISTICS:
     (A) LENGTH: 6
     (B) TYPE: Amino Acids
     (C) STRANDEDNESS:
     (D) TOPOLOGY: Linear (ii) MOLECULE TYPE: Peptide
     (A) DESCRIPTION:

(ix) FEATURE:
     (A) NAME/KEY: 10 × 10 Array Sequence Ligands for
         Streptavidin Test, Address 72.
     (B) LOCATION:
     (C) IDENTIFICATION METHOD: Constructed using an
         Arris Pharmaceutical PILOT Support Array System
     (D) OTHER INFORMATION: Biological activity unknown.
         Xaa represents a random amino acid selected from
         mixtures of the following 10 amino acids to give
         equal incorporation: Nle, His, Pro, Gln, Tyr, Gly,
         Phe, Arg, Glu, Ala. Where Leu or Ala is
         specified at any position in the sequence, then Leu
         refers to Nle (or normal-leucine) and Ala refers to
         Ala (or beta- alanine).

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO: 72: 1 to 6

(xi) SEQUENCE DESCRIPTION: SEQ ID NO: 72:

Xaa Xaa Arg Glu Xaa Xaa
1           5

(2) INFORMATION FOR SEQ ID NO: 73:

(i) SEQUENCE CHARACTERISTICS:
  (A) LENGTH: 6
  (B) TYPE: Amino Acids
  (C) STRANDEDNESS:
  (D) TOPOLOGY: Linear (ii) MOLECULE TYPE: Peptide
  (A) DESCRIPTION:

(ix) FEATURE:
  (A) NAME/KEY: 10 × 10 Array Sequence Ligands for Streptavidin Test, Address 73.
  (B) LOCATION:
  (C) IDENTIFICATION METHOD: Constructed using an Arris Pharmaceutical PILOT Support Array System
  (D) OTHER INFORMATION: Exhibits specific binding activity with Streptavidin. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta-alanine).

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO: 73: 1 to 6

(xi) SEQUENCE DESCRIPTION: SEQ ID NO: 73:

Xaa Xaa Arg Arg Xaa Xaa
1          5

(2) INFORMATION FOR SEQ ID NO: 74:

(i) SEQUENCE CHARACTERISTICS:
  (A) LENGTH: 6
  (B) TYPE: Amino Acids
  (C) STRANDEDNESS:
  (D) TOPOLOGY: Linear (ii) MOLECULE TYPE: Peptide
  (A) DESCRIPTION:

(ix) FEATURE:
  (A) NAME/KEY: 10 × 10 Array Sequence Ligands for Streptavidin Test, Address 74.

(B) LOCATION:
(C) IDENTIFICATION METHOD: Constructed using an
    Arris Pharmaceutical PILOT Support Array System
(D) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, Ala. Where Leu or Ala is
    specified at any position in the sequence, then Leu
    refers to Nle (or normal-leucine) and Ala refers to
    Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 74: 1 to 6

(xi) SEQUENCE DESCRIPTION: SEQ ID NO: 74:

Xaa  Xaa  Arg  Phe  Xaa  Xaa
1                   5

(2) INFORMATION FOR SEQ ID NO: 75:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for
        Streptavidin Test, Address 75.
    (B) LOCATION:
    (C) IDENTIFICATION METHOD: Constructed using an
        Arris Pharmaceutical PILOT Support Array System
    (D) OTHER INFORMATION: Biological activity unknown.
        Xaa represents a random amino acid selected from
        mixtures of the following 10 amino acids to give
        equal incorporation: Nle, His, Pro, Gln, Tyr, Gly,
        Phe, Arg, Glu, Ala. Where Leu or Ala is
        specified at any position in the sequence, then Leu
        refers to Nle (or normal-leucine) and Ala refers to
        Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 75: 1 to 6

(xi) SEQUENCE DESCRIPTION: SEQ ID NO: 75:

Xaa  Xaa  Arg  Gly  Xaa  Xaa
1                   5

(2) INFORMATION FOR SEQ ID NO: 76:

(i) SEQUENCE CHARACTERISTICS:
    (A) LENGTH: 6

(B) TYPE: Amino Acids
                (C) STRANDEDNESS:
                (D) TOPOLOGY: Linear (ii) MOLECULE TYPE: Peptide
                (A) DESCRIPTION:

(ix) FEATURE:
                (A) NAME/KEY: 10 × 10 Array Sequence Ligands for
                        Streptavidin Test, Address 76.
                (B) LOCATION:
                (C) IDENTIFICATION METHOD: Constructed using an
                        Arris Pharmaceutical PILOT Support Array System
                (D) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to
                        Ala (or beta- alanine).

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO: 76: 1 to 6

(xi) SEQUENCE DESCRIPTION: SEQ ID NO: 76:

Xaa     Xaa     Arg     Tyr     Xaa     Xaa
1                               5

(2) INFORMATION FOR SEQ ID NO: 77:

(i) SEQUENCE CHARACTERISTICS:
                (A) LENGTH: 6
                (B) TYPE: Amino Acids
                (C) STRANDEDNESS:
                (D) TOPOLOGY: Linear (ii) MOLECULE TYPE: Peptide
                (A) DESCRIPTION:

(ix) FEATURE:
                (A) NAME/KEY: 10 × 10 Array Sequence Ligands for
                        Streptavidin Test, Address 77.
                (B) LOCATION:
                (C) IDENTIFICATION METHOD: Constructed using an
                        Arris Pharmaceutical PILOT Support Array System
                (D) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to
                        Ala (or beta- alanine).

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO: 77: 1 to 6

( x i ) SEQUENCE DESCRIPTION: SEQ ID NO: 77:

Xaa   Xaa   Arg   Gln   Xaa   Xaa
1                       5

( 2 ) INFORMATION FOR SEQ ID NO: 78:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 78.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 78: 1 to 6

( x i ) SEQUENCE DESCRIPTION: SEQ ID NO: 78:

Xaa   Xaa   Arg   Pro   Xaa   Xaa
1                       5

( 2 ) INFORMATION FOR SEQ ID NO: 79:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 79.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:

( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO: 79: 1 to 6

( x i ) SEQUENCE DESCRIPTION: SEQ ID NO: 79:

Xaa     Xaa     Arg     His     Xaa     Xaa
1                               5

( 2 ) INFORMATION FOR SEQ ID NO: 80:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 × 10 Array Sequence Ligands for
                            Streptavidin Test, Address 80.
                    ( B ) LOCATION:
                    ( C ) IDENTIFICATION METHOD: Constructed using an
                            Arris Pharmaceutical PILOT Support Array System
                    ( D ) OTHER INFORMATION: Biological activity unknown.
                            Xaa represents a random amino acid selected from
                            mixtures of the following 10 amino acids to give
                            equal incorporation: Nle, His, Pro, Gln, Tyr, Gly,
                            Phe, Arg, Glu, Ala. Where Leu or Ala is
                            specified at any position in the sequence, then Leu
                            refers to Nle (or normal-leucine) and Ala refers to
                            Ala (or beta- alanine).

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO: 80: 1 to 6

( x i ) SEQUENCE DESCRIPTION: SEQ ID NO: 80:

Xaa     Xaa     Arg     Leu     Xaa     Xaa
1                               5

( 2 ) INFORMATION FOR SEQ ID NO: 81:

( i ) SEQUENCE CHARACTERISTICS:
                    ( A ) LENGTH: 6
                    ( B ) TYPE: Amino Acids
                    ( C ) STRANDEDNESS:
                    ( D ) TOPOLOGY: Linear ( i i ) MOLECULE TYPE: Peptide
                    ( A ) DESCRIPTION:

( i x ) FEATURE:
                    ( A ) NAME/KEY: 10 × 10 Array Sequence Ligands for
                            Streptavidin Test, Address 81.
                    ( B ) LOCATION:
                    ( C ) IDENTIFICATION METHOD: Constructed using an
                            Arris Pharmaceutical PILOT Support Array System
                    ( D ) OTHER INFORMATION: Biological activity unknown.
                            Xaa represents a random amino acid selected from mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 81: 1 to 6

( x i ) SEQUENCE DESCRIPTION: SEQ ID NO: 81:

Xaa  Xaa  Glu  Ala  Xaa  Xaa
1                   5

( 2 ) INFORMATION FOR SEQ ID NO: 82:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 82.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 82: 1 to 6

( x i ) SEQUENCE DESCRIPTION: SEQ ID NO: 82:

Xaa  Xaa  Glu  Glu  Xaa  Xaa
1                   5

( 2 ) INFORMATION FOR SEQ ID NO: 83:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide (A) DESCRIPTION:

(ix) FEATURE:
  (A) NAME/KEY: 10 × 10 Array Sequence Ligands for
       Streptavidin Test, Address 83.
  (B) LOCATION:
  (C) IDENTIFICATION METHOD: Constructed using an
       Arris Pharmaceutical PILOT Support Array System
  (D) OTHER INFORMATION: Biological activity unknown.
       Xaa represents a random amino acid selected from
       mixtures of the following 10 amino acids to give
       equal incorporation: Nle, His, Pro, Gln, Tyr, Gly,
       Phe, Arg, Glu, Ala. Where Leu or Ala is
       specified at any position in the sequence, then Leu
       refers to Nle (or normal-leucine) and Ala refers to
       Ala (or beta- alanine).

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO: 83: 1 to 6

(xi) SEQUENCE DESCRIPTION: SEQ ID NO: 83:

```
Xaa  Xaa  Glu  Arg  Xaa  Xaa
1                    5
```

(2) INFORMATION FOR SEQ ID NO: 84:

(i) SEQUENCE CHARACTERISTICS:
    (A) LENGTH: 6
    (B) TYPE: Amino Acids
    (C) STRANDEDNESS:
    (D) TOPOLOGY: Linear (ii) MOLECULE TYPE: Peptide
    (A) DESCRIPTION:

(ix) FEATURE:
    (A) NAME/KEY: 10 × 10 Array Sequence Ligands for
         Streptavidin Test, Address 84.
    (B) LOCATION:
    (C) IDENTIFICATION METHOD: Constructed using an
         Arris Pharmaceutical PILOT Support Array System
    (D) OTHER INFORMATION: Biological activity unknown.
         Xaa represents a random amino acid selected from
         mixtures of the following 10 amino acids to give
         equal incorporation: Nle, His, Pro, Gln, Tyr, Gly,
         Phe, Arg, Glu, Ala. Where Leu or Ala is
         specified at any position in the sequence, then Leu
         refers to Nle (or normal-leucine) and Ala refers to
         Ala (or beta- alanine).

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO: 84: 1 to 6

(xi) SEQUENCE DESCRIPTION: SEQ ID NO: 84:

```
Xaa  Xaa  Glu  Phe  Xaa  Xaa
1                    5
```

( 2 ) INFORMATION FOR SEQ ID NO: 85:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 85.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 85: 1 to 6

( x i ) SEQUENCE DESCRIPTION: SEQ ID NO: 85:

```
Xaa    Xaa    Glu    Gly    Xaa    Xaa
1                          5
```

( 2 ) INFORMATION FOR SEQ ID NO: 86:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for
            Streptavidin Test, Address 86.
        ( B ) LOCATION:
        ( C ) IDENTIFICATION METHOD: Constructed using an
            Arris Pharmaceutical PILOT Support Array System
        ( D ) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

( H ) DOCUMENT NUMBER:
            ( I ) FILING DATE:
            ( J ) PUBLICATION DATE:
            ( K ) RELEVANT RESIDUES IN SEQ ID NO: 86: 1 to 6

( x i ) SEQUENCE DESCRIPTION: SEQ ID NO: 86:

Xaa   Xaa   Glu   Tyr   Xaa   Xaa
1                       5

( 2 ) INFORMATION FOR SEQ ID NO: 87:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 87.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to
                        Ala (or beta- alanine).

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO: 87: 1 to 6

( x i ) SEQUENCE DESCRIPTION: SEQ ID NO: 87:

Xaa   Xaa   Glu   Gln   Xaa   Xaa
1                       5

( 2 ) INFORMATION FOR SEQ ID NO: 88:

( i ) SEQUENCE CHARACTERISTICS:
                ( A ) LENGTH: 6
                ( B ) TYPE: Amino Acids
                ( C ) STRANDEDNESS:
                ( D ) TOPOLOGY: Linear ( i i ) MOLECULE TYPE: Peptide
                ( A ) DESCRIPTION:

( i x ) FEATURE:
                ( A ) NAME/KEY: 10 × 10 Array Sequence Ligands for
                        Streptavidin Test, Address 88.
                ( B ) LOCATION:
                ( C ) IDENTIFICATION METHOD: Constructed using an
                        Arris Pharmaceutical PILOT Support Array System
                ( D ) OTHER INFORMATION: Biological activity unknown.
                        Xaa represents a random amino acid selected from
                        mixtures of the following 10 amino acids to give
                        equal incorporation: Nle, His, Pro, Gln, Tyr, Gly,
                        Phe, Arg, Glu, Ala. Where Leu or Ala is
                        specified at any position in the sequence, then Leu
                        refers to Nle (or normal-leucine) and Ala refers to Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 88: 1 to 6

( x i ) SEQUENCE DESCRIPTION: SEQ ID NO: 88:

Xaa  Xaa  Glu  Pro  Xaa  Xaa
1                    5

( 2 ) INFORMATION FOR SEQ ID NO: 89:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 89.
( B ) LOCATION:
( C ) IDENTIFICATION METHOD: Constructed using an
Arris Pharmaceutical PILOT Support Array System
( D ) OTHER INFORMATION: Biological activity unknown.
Xaa represents a random amino acid selected from
mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO: 89: 1 to 6

( x i ) SEQUENCE DESCRIPTION: SEQ ID NO: 89:

Xaa  Xaa  Glu  His  Xaa  Xaa
1                    5

( 2 ) INFORMATION FOR SEQ ID NO: 90:

( i ) SEQUENCE CHARACTERISTICS:
( A ) LENGTH: 6
( B ) TYPE: Amino Acids
( C ) STRANDEDNESS:
( D ) TOPOLOGY: Linear ( i i ) MOLECULE TYPE: Peptide
( A ) DESCRIPTION:

( i x ) FEATURE:
( A ) NAME/KEY: 10 × 10 Array Sequence Ligands for
Streptavidin Test, Address 90.

(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 90: 1 to 6

(xi) SEQUENCE DESCRIPTION: SEQ ID NO: 90:

| Xaa | Xaa | Glu | Leu | Xaa | Xaa |
|---|---|---|---|---|---|
| 1 | | | | 5 | |

(2) INFORMATION FOR SEQ ID NO: 91:

(i) SEQUENCE CHARACTERISTICS:
(A) LENGTH: 6
(B) TYPE: Amino Acids
(C) STRANDEDNESS:
(D) TOPOLOGY: Linear (ii) MOLECULE TYPE: Peptide
(A) DESCRIPTION:

(ix) FEATURE:
(A) NAME/KEY: 10 × 10 Array Sequence Ligands for Streptavidin Test, Address 91.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 91: 1 to 6

(xi) SEQUENCE DESCRIPTION: SEQ ID NO: 91:

| Xaa | Xaa | Ala | Ala | Xaa | Xaa |
|---|---|---|---|---|---|
| 1 | | | | 5 | |

(2) INFORMATION FOR SEQ ID NO: 92:

(i) SEQUENCE CHARACTERISTICS:
(A) LENGTH: 6

(B) TYPE: Amino Acids
(C) STRANDEDNESS:
(D) TOPOLOGY: Linear (i i) MOLECULE TYPE: Peptide
(A) DESCRIPTION:

(i x) FEATURE:
(A) NAME/KEY: 10 × 10 Array Sequence Ligands for Streptavidin Test, Address 92.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 92: 1 to 6

(x i) SEQUENCE DESCRIPTION: SEQ ID NO: 92:

Xaa  Xaa  Ala  Glu  Xaa  Xaa
1                      5

(2) INFORMATION FOR SEQ ID NO: 93:

(i) SEQUENCE CHARACTERISTICS:
(A) LENGTH: 6
(B) TYPE: Amino Acids
(C) STRANDEDNESS:
(D) TOPOLOGY: Linear (i i) MOLECULE TYPE: Peptide
(A) DESCRIPTION:

(i x) FEATURE:
(A) NAME/KEY: 10 × 10 Array Sequence Ligands for Streptavidin Test, Address 93.
(B) LOCATION:
(C) IDENTIFICATION METHOD: Constructed using an Arris Pharmaceutical PILOT Support Array System
(D) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 93: 1 to 6

( x i ) SEQUENCE DESCRIPTION: SEQ ID NO: 93:

Xaa  Xaa  Ala  Arg  Xaa  Xaa
1                   5

( 2 ) INFORMATION FOR SEQ ID NO: 94:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for Streptavidin Test, Address 94.
        ( B ) LOCATION:
        ( C ) IDENTIFICATION METHOD: Constructed using an Arris Pharmaceutical PILOT Support Array System
        ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO: 94: 1 to 6

( x i ) SEQUENCE DESCRIPTION: SEQ ID NO: 94:

Xaa  Xaa  Ala  Phe  Xaa  Xaa
1                   5

( 2 ) INFORMATION FOR SEQ ID NO: 95:

( i ) SEQUENCE CHARACTERISTICS:
        ( A ) LENGTH: 6
        ( B ) TYPE: Amino Acids
        ( C ) STRANDEDNESS:
        ( D ) TOPOLOGY: Linear ( i i ) MOLECULE TYPE: Peptide
        ( A ) DESCRIPTION:

( i x ) FEATURE:
        ( A ) NAME/KEY: 10 × 10 Array Sequence Ligands for Streptavidin Test, Address 95.
        ( B ) LOCATION:
        ( C ) IDENTIFICATION METHOD: Constructed using an Arris Pharmaceutical PILOT Support Array System
        ( D ) OTHER INFORMATION: Biological activity unknown. Xaa represents a random amino acid selected from mixtures of the following 10 amino acids to give equal incorporation: Nle, His, Pro, Gln, Tyr, Gly, Phe, Arg, Glu, Ala. Where Leu or Ala is specified at any position in the sequence, then Leu refers to Nle (or normal-leucine) and Ala refers to Ala (or beta- alanine).

( x ) PUBLICATION INFORMATION:
        ( A ) AUTHORS:
        ( B ) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO: 95: 1 to 6

(xi) SEQUENCE DESCRIPTION: SEQ ID NO: 95:

Xaa Xaa Ala Gly Xaa Xaa
1               5

(2) INFORMATION FOR SEQ ID NO: 96:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for
            Streptavidin Test, Address 96.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from
            mixtures of the following 10 amino acids to give
            equal incorporation: Nle, His, Pro, Gln, Tyr, Gly,
            Phe, Arg, Glu, Ala. Where Leu or Ala is
            specified at any position in the sequence, then Leu
            refers to Nle (or normal-leucine) and Ala refers to
            Ala (or beta- alanine).

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 96: 1 to 6

(xi) SEQUENCE DESCRIPTION: SEQ ID NO: 96:

Xaa Xaa Ala Tyr Xaa Xaa
1               5

(2) INFORMATION FOR SEQ ID NO: 97:

(i) SEQUENCE CHARACTERISTICS:
        (A) LENGTH: 6
        (B) TYPE: Amino Acids
        (C) STRANDEDNESS:
        (D) TOPOLOGY: Linear (ii) MOLECULE TYPE: Peptide
        (A) DESCRIPTION:

(ix) FEATURE:
        (A) NAME/KEY: 10 × 10 Array Sequence Ligands for
            Streptavidin Test, Address 97.
        (B) LOCATION:
        (C) IDENTIFICATION METHOD: Constructed using an
            Arris Pharmaceutical PILOT Support Array System
        (D) OTHER INFORMATION: Biological activity unknown.
            Xaa represents a random amino acid selected from mixtures of the following 10 amino acids to give
equal incorporation: Nle, His, Pro, Gln, Tyr, Gly,
Phe, Arg, Glu, Ala. Where Leu or Ala is
specified at any position in the sequence, then Leu
refers to Nle (or normal-leucine) and Ala refers to
Ala (or beta- alanine).

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO: 97: 1 to 6

( x i ) SEQUENCE DESCRIPTION: SEQ ID NO: 97:

Xaa Xaa Ala Gln Xaa Xaa
1           5

( 2 ) INFORMATION FOR SEQ ID NO: 98:

( i ) SEQUENCE CHARACTERISTICS:
  ( A ) LENGTH: 6
  ( B ) TYPE: Amino Acids
  ( C ) STRANDEDNESS:
  ( D ) TOPOLOGY: Linear ( i i ) MOLECULE TYPE: Peptide
  ( A ) DESCRIPTION:

( i x ) FEATURE:
  ( A ) NAME/KEY: 10 × 10 Array Sequence Ligands for
    Streptavidin Test, Address 98.
  ( B ) LOCATION:
  ( C ) IDENTIFICATION METHOD: Constructed using an
    Arris Pharmaceutical PILOT Support Array System
  ( D ) OTHER INFORMATION: Biological activity unknown.
    Xaa represents a random amino acid selected from
    mixtures of the following 10 amino acids to give
    equal incorporation: Nle, His, Pro, Gln, Tyr, Gly,
    Phe, Arg, Glu, Ala. Where Leu or Ala is
    specified at any position in the sequence, then Leu
    refers to Nle (or normal-leucine) and Ala refers to
    Ala (or beta- alanine).

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO: 98: 1 to 6

( x i ) SEQUENCE DESCRIPTION: SEQ ID NO: 98:

Xaa Xaa Ala Pro Xaa Xaa
1           5

( 2 ) INFORMATION FOR SEQ ID NO: 99:

( i ) SEQUENCE CHARACTERISTICS:
  ( A ) LENGTH: 6
  ( B ) TYPE: Amino Acids
  ( C ) STRANDEDNESS:
  ( D ) TOPOLOGY: Linear ( i i ) MOLECULE TYPE: Peptide ( A ) DESCRIPTION:

( i x ) FEATURE:
            ( A ) NAME/KEY: 10 × 10 Array Sequence Ligands for
                    Streptavidin Test, Address 99.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, Ala. Where Leu or Ala is
                    specified at any position in the sequence, then Leu
                    refers to Nle (or normal-leucine) and Ala refers to
                    Ala (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 99: 1 to 6

( x i ) SEQUENCE DESCRIPTION: SEQ ID NO: 99:

Xaa   Xaa   Ala   His   Xaa   Xaa
1                       5

( 2 ) INFORMATION FOR SEQ ID NO: 100:

( i ) SEQUENCE CHARACTERISTICS:
            ( A ) LENGTH: 6
            ( B ) TYPE: Amino Acids
            ( C ) STRANDEDNESS:
            ( D ) TOPOLOGY: Linear ( i i ) MOLECULE TYPE: Peptide
            ( A ) DESCRIPTION:

( i x ) FEATURE:
            ( A ) NAME/KEY: 10 × 10 Array Sequence Ligands for
                    Streptavidin Test, Address 100.
            ( B ) LOCATION:
            ( C ) IDENTIFICATION METHOD: Constructed using an
                    Arris Pharmaceutical PILOT Support Array System
            ( D ) OTHER INFORMATION: Biological activity unknown.
                    Xaa represents a random amino acid selected from
                    mixtures of the following 10 amino acids to give
                    equal incorporation: Nle, His, Pro, Gln, Tyr, Gly,
                    Phe, Arg, Glu, Ala. Where Leu or Ala is
                    specified at any position in the sequence, then Leu
                    refers to Nle (or normal-leucine) and Ala refers to
                    Ala (or beta- alanine).

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO: 100: 1 to 6

( x i ) SEQUENCE DESCRIPTION: SEQ ID NO: 100:

Xaa   Xaa   Ala   Leu   Xaa   Xaa
1                       5

(2) INFORMATION FOR SEQ ID NO: 101:

(i) SEQUENCE CHARACTERISTICS:
  (A) LENGTH: 8
  (B) TYPE: Amino Acids
  (C) STRANDEDNESS:
  (D) TOPOLOGY: Linear (ii) MOLECULE TYPE: Peptide
  (A) DESCRIPTION:

(ix) FEATURE:
  (A) NAME/KEY: Pepsyn-K Bead Test Peptide
  (B) LOCATION:
  (C) IDENTIFICATION METHOD: Constructed using a
   Milligen/Biosearch Model 9600 peptide synthesizer.
  (D) OTHER INFORMATION: Biological activity not
   determined. Xaa represents a random amino acid
   selected from mixtures of the following 10 amino
   acids to give equal incorporation: Nle, His, Pro,
   Gln, Tyr, Gly, Phe, Arg, Glu, Ala. Where Leu or
   Ala is specified at any position in the sequence,
   then Leu refers to Nle (or normal-leucine) and Ala
   refers to Ala (or beta-alanine).

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO: 101: 1 to 8

(xi) SEQUENCE DESCRIPTION: SEQ ID NO: 101:

```
Ala    Ala    Ala    Leu    Ala    Leu    Ala    Ala
1                           5
```

We claim:

1. A method of synthesizing chemical polymer sequences on a continuous support substrate comprising the steps of:

(a) providing a reusable substrate plate having an ordered array of separated, discrete areas thereon which areas are functionalized so as to be reactive with at least one protected monomer contacted therewith;

(b) superimposing on said substrate plate a first block having a first top and a first bottom and a plurality of first slots disposed to extend vertically between said first top and bottom, each of said first slots being aligned with a first set of a plurality of said discrete areas in said ordered array to permit access thereto of a common monomer for simultaneous reaction with all of said first set of discrete areas aligned with and accessible via a given slot;

(c) adding a first solution of a preselected protected monomer to each of the first slots of said first block wherein the solution added to each slot is selected from a plurality of solutions, wherein each solution in said plurality of solutions comprises a different known protected monomer, said protected known monomer having a terminal functional group which reacts with the functionalized discrete areas of the substrate plate;

(d) reacting each of said first preselected protected monomer solutions with the sets of discrete areas of said substrate plate to attach the protected monomers in said monomer solutions to said sets of the discrete areas of said substrate to form a reacted substrate having a plurality of sets of reacted discrete areas each with a protected first monomer attached thereto;

(e) deprotecting the protected first monomers attached to said reacted substrate to provide a deprotected first monomer;

(f) removing said first block from said substrate;

(g) superimposing on said substrate a second block having a second top and a second bottom and a plurality of second slots disposed to extend vertically between said second top and bottom, said second block being oriented with its plurality of second slots aligned orthogonally to the direction of said plurality of first slots of said first block, each of said second slots being aligned with a second set of a plurality of discrete areas oriented orthogonally with respect to said first set of areas to permit access thereto of a common monomer for simultaneous reaction with all of said deprotected first monomers on said second set of discreet areas;

(h) adding a second solution of a preselected protected monomer to each of said second slots of said second block, wherein the solution added to each slot is selected from a plurality of solutions, wherein each solution in said plurality of solutions comprises a different known protected monomer, said monomers having corresponding terminal functional groups which react with said first plurality of preselected deprotected first monomers;

(i) reacting the second preselected protected monomer solutions with the deprotected first monomers attached to said second sets of reacted discreet areas on said substrate to attach the second protected monomer to the first deprotected monomers; and (j) deprotecting said protected second monomer to form a deprotected array of discreet areas having polymer sequences of known monomers in known positions in said polymer sequences at known address locations in said array of areas to provide an Addressable Synthetic Biopolymer Combinatorial Library (ASBCL).

2. The method of claim 1 wherein said plurality of first slots is a plurality of linear parallel slots.

3. The method of claim 2 wherein said plurality of second slots is a plurality of linear parallel slots.

4. The method of claim 3 wherein the step of superimposing on the reacted substrate said second block with said plurality of second slots being orthogonal to said plurality of first slots is performed by rotating said first block 90°.

5. The method of claim 1 wherein said plurality of first and second slots are selected from a plurality of concentric annular slots or a plurality of linear radial slots.

6. The method of claim 1 wherein in the step of reacting the protected monomer solutions with the substrate there is a different monomer solution in each slot, which are reacted simultaneously.

7. The method of claim 1 wherein other known moieties having terminal functional groups which react with said second deprotected monomers are introduced to said polymer sequences at specific addresses of said array or randomly among said array addresses by reacting said moieties with said deprotected second monomers, which is repeated until a preselected polymer length or size is achieved:

wherein the introduction of a known protected moiety at a specific address comprises the additional steps of repeating steps (g), (h), (i) and (j) using said known protected moiety; and wherein the introduction of known protected moieties at random addresses comprising the additional steps of:

(i) providing a solution of a mixture of protected known moieties having terminal functional groups which react with said second deprotected monomers, said known moieties being present in said mixtures in predetermined amounts to provide for substantially equal incorporation during polymer assembly;

(ii) providing a border frame assembly to form a central well to permit simultaneous reaction of all of the deprotected monomers attached to said discrete areas of a selected array with known protected moieties in said protected moiety mixture solution;

(iii) contacting the entirety of said deprotected monomers attached to said discrete areas with said known protected moiety mixture to react said deprotected monomers with said known protected moiety mixture to provide substantially random and equal incorporation of individual protected moieties in said known protected moiety mixture into said polymer sequence at each of said discreet areas of the array; and (iv) deprotecting said protected moieties to form a deprotected array of areas having polymer sequences of known moieties in known polymer sequence positions and unknown members of a known moiety mixture in known positions in said polymer sequences at known address locations in said array of areas to provide an Addressable Synthetic Biopolymer Combinatorial Library (ASBCL).

8. The method of claim 7 wherein said protected moieties in said protected moiety mixture are selected from the group consisting of protected L-amino acids, D-amino acids, non-natural amino acids, and mixtures thereof; protected DNA monomers, protected RNA monomers, and mixtures thereof, wherein said DNA and RNA monomers are natural and unnatural bases.

9. The method of claim 7 wherein the positions in said polymer sequence other than those occupied by said known monomers are selected from the group consisting of random moieties having terminal functional groups reactive with said known deptrotected monomers; and polymers composed of moieties having terminal functional groups reactive with said known deprotected monomers, wherein said monomers and said polymers are present in concentration providing equal incorporation into the polymer sequence.

10. The method of claim 1 wherein said first and said second protected known monomers attached in said polymer sequence are sequential to each other or separated by other moieties.

11. The method of claim 9 wherein said randomly incorporated moieties are selected from the group consisting of protected L-amino acids, D-amino acids, non-natural amino acids, and mixtures thereof; protected DNA monomers, protected RNA monomers, and mixtures thereof, wherein said DNA and RNA monomers are natural and unnatural bases.

12. The method of claim 11 wherein said monomers are L-amino acids, D-amino acids or non-natural amino acids.

13. The method of claim 12 wherein the positions in said polymer sequence other than occupied by said known amino acids are selected from the group consisting of random equimolar mixed amino acids, dipeptides, tripeptides and polypeptides.

14. The method of claim 12 wherein said monomers are L- amino acids.

15. The method of claim 14 wherein said sequence is a hexapeptide forming an Addressable Synthetic Peptide Combinatorial Library.

16. The method of claim 1 which includes the added steps of:

(k) screening said array of polymer sequences having two known monomers in any known positions against a preselected target molecule to locate by address in said array on said substrate at least one polymer sequence which binds to the preselected target molecule;

(l) determining the known monomer sequence by reference to the address in said array on said substrate;

(m) repeating the steps of reacting protected known monomers at determined positions in said polymer sequence different than the positions of said first and second known monomers to form a second array;

(n) repeating said screening against said preselected target molecule;

(o) repeating said determination of known monomer sequences; and (p) repeating steps (m), (n) and (o) at least one additional time to fully characterize the polymer sequence which binds to said target molecule.

17. The method of claim 16 wherein said protected known monomers attached in said polymer sequence are sequential to each other or separated by said other moieties.

18. The method as in claim 17 wherein said other moieties are selected from the group consisting of random equimolar mixtures of monomers and polymers, wherein said random mixtures of monomers or polymers have terminal functional groups reactive with said second deprotected monomers.

19. The method of claim 18 wherein said randomly incorporated moieties are selected from the group consisting of protected L-amino acids, D-amino acids, non-natural amino acids, and mixtures thereof; protected DNA monomers, protected RNA monomers, and mixtures thereof, wherein said DNA and RNA monomers are natural and unnatural bases.

20. The method of claim 19 wherein said monomers are L-amino acids, D-amino acids or non-natural amino acids.

21. A method of claim 20 wherein said amino acids are L-amino acids.

22. A method of claim 21 wherein said sequence is a hexapeptide forming an Addressable Synthetic Peptide Combinatorial Library.

23. The method of claim 1 further comprising steps for the assay of binding of biologically active target molecules, comprising the additional steps of:
  (k) exposing said ASBCL plate to at least one solution expected to contain at least one target molecule; and
  (l) identifying any target molecule in said solution which binds to an address on said array.

24. A method as in claim 23 wherein said ASBCL plate array includes at least some peptide sequences thereon.

25. A method as in claim 23 wherein said ASBCL is an Addressable Synthetic Peptide Combinatorial. Library.

* * * * *